United States Patent [19]

Shaver et al.

[11] Patent Number: 5,064,946

[45] Date of Patent: Nov. 12, 1991

[54] THERAPEUTIC NUCLEOSIDES

[75] Inventors: Sammy R. Shaver, Chapel Hill; George A. Freeman; Janet L. Rideout, both of Raleigh, all of N.C.

[73] Assignee: Burroughs Wellcome Co., Research Triangle Park, N.C.

[21] Appl. No.: 453,013

[22] Filed: Dec. 20, 1989

Related U.S. Application Data

[63] Continuation of Ser. No. 168,181, Mar. 15, 1988, abandoned.

[30] Foreign Application Priority Data

Mar. 16, 1987 [GB] United Kingdom ............... 8706176

[51] Int. Cl.$^5$ ............................................. C07H 17/00
[52] U.S. Cl. ........................................................ 536/23
[58] Field of Search ...................... 536/23; 514/49, 50

[56] References Cited

U.S. PATENT DOCUMENTS 4,594,339  6/1986  Lopez et al. .................... 514/49
4,681,933  7/1987  Chu et al. ........................ 536/23

OTHER PUBLICATIONS

DeClercq, Expt. Clin. Pharm. 2(5):253–63, 1980.
Imazawa et al., J. Org. Chem. 43(15):3044–3048, 1978.
Yarchogn et al., The Lance, Mar. 15, 1986, pp. 575–580.

*Primary Examiner*—John W. Rollins
*Attorney, Agent, or Firm*—Donald Brown; David S. Resnick

[57] ABSTRACT

Several novel 3-azido-2,3-dideoxy-β-D-erythro-pentofuranosyl derivatives of substituted pyrimidinones having antiretroviral, especially anti-AIDS, activity are described.

1 Claim, No Drawings

THERAPEUTIC NUCLEOSIDES

This is a continuation of copending application Ser. No. 07/168,181 filed on Mar. 15, 1988, now abandoned.

The present invention relates to 3'-azido-nucleosides, pharmaceutically acceptable derivatives thereof, combinations containing them, and their use in therapy, particularly for the treatment or prophylaxis of certain viral and bacterial infections.

In the field of antiviral chemotherapy, few drugs exist which effectively combat the virus per se, owing to the difficulty of attacking the virus while leaving uninfected host cells unimpaired. It was long supposed that, with the extreme parasitic nature of viruses, all the necessary facilities for viral replication were provided by the host cell. It has recently been established that certain stages in the virus life-cycle, which vary from species to species, are specified by the virus itself, and these stages may prove susceptible to attack where they differ sufficiently from any corresponding host-cell function. However, owing to great similarity between viral and host functions, effective treatments have proven very difficult to identify.

For this reason, compounds identified as being suitable for the treatment of viral infections usually have some toxicity for the host. Thus, the ideal medication is non-toxic at antivirally effective concentrations but, in the absence of such a treatment, the compound should possess a good therapeutic ratio, that is, the concentrations at which the treatment is toxic are significantly higher than those at which an antiviral activity is observed.

One group of viruses which has recently assumed a particular importance are the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome may be incorporated into the host cell genome, allowing it to take full advantage of the host cell's transcription/translation machinery for the purposes of replication. Once incorporated, the viral DNA is virtually indistinguishable from the host's DNA and, in this state, the virus may persist for as long as the cell lives. As it is virtually invulnerable to attack in this form, any treatment must be directed at another stage of the virus life cycle and will, of necessity, have to be continued until all virus-infected cells have died.

HTLV-I and HTLV-II are both retroviruses and are known to be causative agents of leukaemia in man. HTLV-I infections are especially widespread and are responsible for many deaths world-wide each year.

A species of retrovirus has also been reproducibly isolated from patients with AIDS. While it has been extensively characterised, there is still some dispute as to an internationally agreeable name for the virus. It is currently known either as human T-cell lymphotropic virus III (HTLV III), AIDS associated retrovirus (ARV), or lymphadenopathy associated virus (LAV) but it is anticipated that the name to be agreed on internationally will be human immunodeficiency virus (HIV). This virus (referred to herein as HIV) has been shown preferentially to infect and destroy T-cells bearing the OKT4 surface marker and is now generally accepted as the aetiologic agent of AIDS. The patient progressively loses this set of T-cells, upsetting the overall balance of the immune system, reducing his ability to combat other infections, and predisposing him to opportunistic infections which frequently prove fatal. Thus, the usual cause of death in AIDS victims is by opportunistic infection, such as pneumonia or cancers which may be virally induced, and not necessarily as a direct result of HIV infection. Other conditions associated with HIV infection include thrombocytopaenia purpura and Kaposi's sarcoma.

Recently, HIV has also been recovered from other tissue types, including B-cells expressing the T4 marker, macrophages and non-blood associated tissue in the central nervous system. This infection of the central nervous system is not necessarily associated with classical AIDS and has been found in patients with asymptomatic HIV infections. HIV infection of the CNS is associated with progressive demyelination, leading to wasting and such symptoms as encephalopathy, progressive dysarthria, ataxia and disorientation. Further conditions associated with HIV infection are the asymptomatic carrier state, progressive generalised lymphadenopathy (PGL) and AIDS-related complex (ARC).

It is now considered that certain, chronic, neurological infections are caused by retroviruses. Such infections include multiple sclerosis in man, for example, and caprine arthritis encephalitis virus infections in goats, and visna-maedi infections in sheep.

Reports have described the testing of compounds against various retroviruses, for example, Friend Leukaemia Virus (FLV), a murine retrovirus. For instance Krieg et al. (Exp. Cell Res., 116 (1978) 21-29) found 3'-azido-3'-deoxythymidine to be active against FLV in in vitro experiments, and Ostertag et al. (Proc. Nat. Acad. Sci. (1974) 71, 4980-85) stated that, on the basis of antiviral activity related to FLV and a lack of cellular toxicity, 3'-azido-3'-dideoxythymidine "might favourably replace bromodeoxyuridine for medical treatment of diseases caused by DNA viruses". However, De Clerq et al. (Biochem. Pharm. (1980) 29, 1849–1851) established, six years later, that 3'-azido-3'-dideoxythymidine had no appreciable activity against any viruses used in their tests, including such DNA viruses as vaccinia, HSVI and varicella zoster virus (VZV).

Bacteria also present a problem in therapy, as all living organisms employ very much the same life processes as one another, so a substance toxic to one is likely to prove toxic to another. In addition, experience has shown that, in time, strains of bacteria develop that are resistant to the commonly used antibacterial agents.

It has now been found that certain 3'-azidonucleosides as described below are useful in the therapy of viral and bacterial infections, particularly retroviral infections, including HIV infections and gram-negative bacterial infections, including certain strains of gram-negative bacteria resistant to commonly used antibacterial agents.

Thus, in a first aspect of the present invention, there is provided a compound of formula

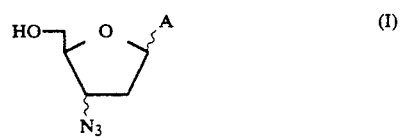

wherein A is a purine or pyrimidine base, other than thymine, linked at the 9- or 1-position, or a pharmaceutically acceptable derivative thereof, for use in human or veterinary therapy.

The compounds of formula (I) and their pharmaceutically acceptable derivatives are referred to herein as the compounds according to the invention.

Retroviral infections frequently affect the central nervous system of the subject and, in this connection, a particular advantage of the compounds according to the invention is as, experiments have demonstrated, their ability to cross the blood-brain barrier in clinically effective quantities.

The compounds according to the invention have been found to possess particularly potent activity against retroviral and gram-negative bacterial infections.

Accordingly, there is provided (a) the compounds according to the invention for use in the treatment or prophylaxis of retroviral or gram-negative bacterial infections and (b) use of the compounds according to the invention in the manufacture of a medicament for the treatment or prophylaxis of a retroviral or gram-negative bacterial infection.

The term "retroviral infections", as used herein, refers to any virus which, for an integral part of its life-cycle, employs a reverse transcriptase.

Particular bacteria against which good activity has been found are as follows.

*Escherichia coli, Salmonella dublin, Salmonella typhosa, Salmonella typhimurium, Shigella flexneri, Citrobacter freundii, Klebsiella pneumoniae, Vibrio cholerae, Vibrio anquillarum, Enterobacter aerogenes, Pasteurella multocida, Haemophilus influenzae, Yersinia enterocolitica, Pasteurella haemolytica, Proteus mirabilis* and *Proteus vulgaris*, the causative organisms of such ailments as travellers' diarrhoea, urinary tract infections, shigellosis, typhoid fever and cholera in humans, as well as animal diseases such as calf neonatal enteritis, pig post-weaning enteritis and chicken colisepticaemia.

The compounds according to the invention are useful in the treatment of psoriasis.

The compounds according to the invention have particularly good activity against the following viruses: human T-cell lymphotropic viruses (HTLV), especially HTLV-I, HTLV-II and HTLV-III (HIV); feline leukaemia virus, equine infectious anaemia virus, caprine arthritis virus and other lentiviruses, as well as other human viruses such as hepatitis B virus, Epstein-Barr virus (EBV) and the causative agent of multiple sclerosis (MS). The compounds according to the invention have also been found to be effective in the treatment of Kaposi's sarcoma (KS) and thrombocytopaenia purpura (TP). For these last indications (MS, KS and TP) and caprine arthritis virus, the present invention includes the compounds of formula (I), wherein A is thymine, for use in their treatment or prophylaxis, as well as the use of such compounds in the manufacture of a medicament for their treatment or prophylaxis.

The activity of the compounds according to the invention against such a wide range of bacterial and viral infections is clearly of great advantage in medicine, and the novel mode of action allows the use of these compounds in combination therapy to reduce the chance of resistance developing. However, such combinations are particularly useful, as the 3'-azidonucleosides have a surprising capacity for potentiation by other therapeutic agents as described below.

It has been discovered that 3'-azidonucleosides cooperate synergistically with a wide range of other therapeutic agents, thereby disproportionately enhancing the therapeutic potential of both agents. Significantly less of each compound is required for treatment, the therapeutic ratio is raised and, accordingly, the risk of toxicity from either compound is reduced.

Therefore, according to a further aspect of the present invention, there is provided a compound of formula

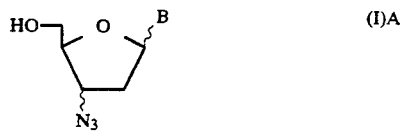

(I)A wherein B is a purine or pyrimidine base linked at the 9- or 1-position respectively, or a pharmaceutically acceptable derivative thereof, for use in combination therapy with at least one further therapeutic agent.

In particular, there is provided a compound of formula (I)A, or a pharmaceutically acceptable derivative thereof, for use in combination therapy as described above, wherein the two active agents are present in a potentiating ratio.

A "potentiating ratio" is that ratio of the compound of formula (I)A, or a pharmaceutically acceptable derivative thereof, to the second therapeutic agent which provides a therapeutic effect greater than the sum of the therapeutic effects of the individual components.

It will be appreciated that, while there will usually be an optimum ratio to ensure maximum potentiation, even a vanishingly small quantity of one agent will suffice to potentiate the effect of the other to some degree, and so any ratio of two potentiating drugs will still possess the required synergistic effect. However, greatest synergy is observed when the two agents are present in a ratio of 500:1 to 1:500, preferably 100:1 to 1:100, particularly 20:1 to 1:20 and especially 10:1 to 1:10.

The present invention, therefore, further provides a therapeutic combination of a compound of formula (I)A, or a pharmaceutically acceptable derivative thereof, and at least one further therapeutic agent.

The combinations described above are referred to herein as combinations according to the invention.

Thus, there is further provided a combination according to the invention for use in the treatment or prophylaxis of, or use of such combinations in the manufacture of a medicament for the treatment or prophylaxis of, any of the infections or indications mentioned above.

The combinations according to the invention may conveniently be administered together, for example, in a unitary pharmaceutical formulation, or separately, for example as a combination of tablets and injections administered at the same time or different times, in order to achieve the required therapeutic effect.

In antiviral tests, it has been found that, for example, azidonucleosides are potentiated by such diverse agents as interferons, nucleoside transport inhibitors, glucuronidation inhibitors, renal excretion inhibitors and even other therapeutic nucleosides which may not necessarily have activity against the same organisms as the compounds of formula (I)A.

Particularly preferred types of interferon are α, β and γ while nucleoside transport inhibitors include such agents as dilazep, dipyridamole, 6-[(4-nitrobenzoyl)thio]-9-(β-D-ribofuranosyl) purine, papavarine, mioflazine, hexobendine, lidoflazine and their acid addition salts.

Probenecid is particularly useful in combination with the 3'-azidonucleosides of formula (I)A, as it possesses both renal excretion inhibiting activity and glucuronidation blocking activity. Examples of other compounds useful in this aspect include acetaminophen, aspirin, lorazepam, cimetidine, ranitidine, zomepirac, clofibrate, indomethacin, ketoprofen, naproxen and other compounds which compete for glucuronidation or otherwise undergo significant glucuronidation.

3'-azidonucleosides of formula I(A) and their pharmaceutically acceptable derivatives are potentiated by other therapeutic nucleoside derivatives as described above, including acyclic nucleosides of the type described for example in UK Patent Specification No. 1 523 865, U.S. Pat. No. 4,360,522, European Patent Specifications 74 306, 55 239 and 146 516, and European Patent Applications 434 393 and 434 395, and particularly include those compounds of the general formula

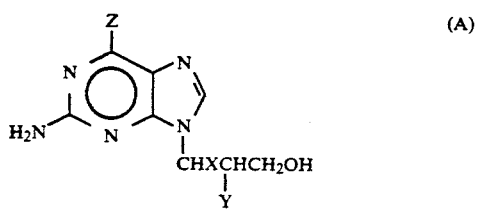

(A)

wherein Z represents a hydrogen atom or a hydroxy or amino group;
  X represents
    (a) an oxygen or sulphur atom or a methylene group and Y represents a hydrogen atom or a hydroxymethylene group; or
    (b) methyleneoxy group (—OCH$_2$) and Y represents a hydroxy group;
  and pharmaceutically acceptable derivatives thereof.

Examples of the above-mentioned derivatives are salts and esters and include base salts e.g. alkali metal (e.g. sodium) or alkaline earth metal salts and pharmaceutically acceptable salts of organic acids such as lactic, acetic, malic or p-toluenesulphonic acid, as well as pharmaceutically acceptable salts of mineral acids such as hydrochloric or sulphuric acid.

Esters of the compounds of formula (A) which may be conveniently used in accordance with the present invention include those containing a formyloxy or C$_{1-16}$ (for example C$_{1-6}$)alkanoyloxy (e.g. acetoxy or propionyloxy), optionally substituted aralkanoyloxy (e.g. phenyl-C$_{1-4}$alkanoyloxy such as phenyl-acetoxy) or optionally substituted aroyloxy (e.g. benzoyloxy or naphthoyloxy) ester grouping at one or both of the terminal positions of the 9-side chain of the compounds of formula (A). The above-mentioned aralkanoyloxy and aroyloxy ester groups may be substituted, for example, by one or more halogen (e.g. chlorine or bromine) atoms or amino, nitrile or sulphamido groups, the aryl moiety of the grouping advantageously containing 6 to 10 carbon atoms.

Particularly preferred examples of compounds of the above general formula (A) for use in accordance with the present invention include 9-[(2-hydroxy-1-hydroxymethylethoxy)methyl]guanine, 2-amino-9-(2-hydroxyethoxymethyl)purine and particularly 9-(2-hydroxyethoxymethyl)guanine (acyclovir). The latter compound has been found to have a particularly good potentiating effect, especially when the compound of formula I(A) is 3'-azido-3'-deoxythymidine, as described in the examples.

In the antibacterial field, it has also been found that a broad spectrum of antibiotics is effective in potentiating the activity of azidonucleosides. These include diverse agents such as: benzylpyrimidines e.g. 2,4-diamino-5-(3',4',5'-trimethoxybenzyl) pyrimidine (Trimethoprim) and analogues thereof, for example as described in UK Patent Specification No. 1 405 246; sulphonamides e.g. sulfadimidine; rifampicin; tobramycin; fusidic acid; chloramphenicol; clindamycin and erythromycin.

Thus, in a further aspect there is provided combinations according to the invention wherein the second agent is at least one of the above-mentioned antiviral or antibacterial agents or classes of agent.

Other combinations suitable for use according to the present invention include those wherein the second agent is, for example, interleukin II, suramin, phosphonoformate, HPA 23, 2',3'-dideoxynucleosides, for example, 2',3'-dideoxycytidine and 2',3'-dideoxyadenosine, or medications such as levamisol or thymosin to increase lymphocyte numbers and/or function as appropriate, also including granulocyte macrophage colony stimulating factor.

It will further be appreciated that the compounds and combinations according to the invention may also be used in conjunction with other immune modulating therapy including, for example, bone marrow and lymphocyte transplants.

Certain of the retroviral infections described above, for example AIDS, are commonly associated with opportunistic infections. Thus, it will be appreciated that, for example, a combination of 3'-azido-3'-deoxythymidine (AZT) and acyclovir would prove particularly useful in the treatment of an AIDS patient with an opportunistic herpes infection, while a combination of AZT and 9-[(2-hydroxy-1-hydroxymethylethoxy)methyl]guanine would be useful in the treatment of an AIDS patient with an opportunistic cytomegalovirus infection.

Generally preferred pyrimidines of formula (I) and (I)A for use according to the present invention are those of the formula:

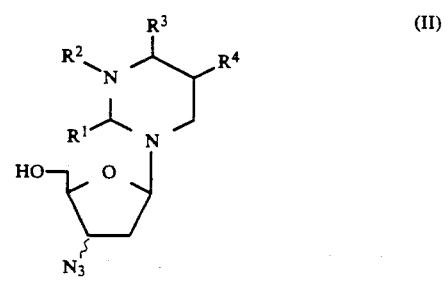

(II)

wherein
  R$^1$ is hydroxy, mercapto, amino, alkylthio, aralkoxy, alkoxy, cyano, alkylamino, dialkylamino, the alkyl groups optionally linked to form a heterocycle;
  R$^2$ is hydrogen, acyl, alkyl, aroyl or sulphonate;
  R$^3$ is hydroxy, mercapto, amino, triazolyl, alkylamino, dialkylamino, the alkyl groups being optionally linked to form a heterocycle, aralkoxy, alkoxy, alkylthio or hydrogen;

$R^4$ is alkyl, substituted alkyl, halo, perhalomethyl, hydroxy, alkoxy, cyano, nitro, alkenyl, substituted alkenyl, alkynyl, substituted alkynyl or hydrogen; and pharmaceutically acceptable derivatives thereof.

In the above general formula (I) the dotted lines in the 2- to 6- positions are intended to indicate the presence of single or double bonds in these positions the relative positions of the single and double bonds being determined by whether the substituents $R^1$ and $R^2$ are groups capable of e.g. keto-enol tautomerism.

Preferred classes of pyrimidine nucleoside according to the invention are cytidine derivatives, e.g. compounds of formula (II) wherein $R^3$ is amino or alkylamino, particularly wherein the 3' azido group is in the erythro configuration ("down azido"); thymidine and uridine derivatives (e.g. compounds of formula (I) wherein $R^3$ is other than amino or alkylamino) wherein the 3' azido is in either the erythro or threo ("up azido") configuration; and nucleosides unsaturated between the 5C and 6C positions.

Generally preferred purines of formulae (I) and (I)A for use according to the present invention are of the formula

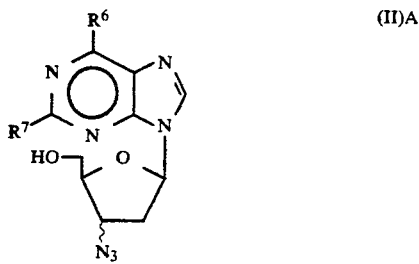

(II)A wherein $R^6$ and $R^7$ may be the same or different and are selected from amino, hydrogen, hydroxy, mercapto, alkylthio, alkoxy, aralkoxy, cyano or alkylamino; and pharmaceutically acceptable derivatives thereof.

Preferred classes of purine nucleoside according to the invention are adenine derivatives, e.g. compounds of formula (II)A wherein $R^6$ is amino or substituted amino, and guanine derivatives, e.g. compounds of formula (III) wherein $R^6$ is as defined, other than amino or substituted amino, and $R^7$ is amino or substituted amino.

The above-mentioned acyl groups advantageously comprise alky or aryl groups as described below. With regard to the compounds of formulae (II) and (II)A above, the above-mentioned alkyl groups advantageously contain 1 to 8 carbon atoms, particularly 1 to 4 carbon atoms, e.g. methyl or ethyl groups, optionally substituted by one or more appropriate substituents, as described below. The above-mentioned aryl groups including the aryl moieties of such groups as aralkoxy are preferably phenyl groups optionally substituted by one or more appropriate substituents, as described below. The above-mentioned alkenyl and alkynyl groups advantageously contain 2 to 8, particularly 2 to 4, carbon atoms, e.g. ethenyl or ethynyl, optionally substituted by one or more appropriate substituents as described below.

Appropriate substituents on the above-mentioned alkyl, alkenyl, alkynyl and aryl groups are advantageously selected from halogen, hydroxy, $C_{1-4}$ alkoxy, $C_{1-4}$ alkyl, $C_{6-12}$ aryl, $C_{6-12}$ aralkoxy, carboxy, amino and substituted amino wherein the amino is singly or doubly substituted by a $C_{1-4}$ alkyl, and when doubly substituted, the alkyl groups optionally being linked to form a heterocycle.

Further classes of preferred compounds of formula (II) include those wherein one or more of $R^1$, $R^2$, $R^3$ and $R^4$ are as defined below, namely $R^1$ is hydroxy, mercapto, $C_{1-4}$ alkoxy or amino;
$R^2$ is hydrogen, methyl, $C_{1-2}$ alkanoyl or benzoyl;
$R^3$ is hydroxy, mercapto, amino, substituted amino or hydrogen;
$R^4$ is hydrogen, when $R^3$ is amino or substituted amino, and halogen, perhalomethyl, $C_{2-3}$ alkyl, $C_{2-3}$ alkenyl or substituted ethenyl when $R^3$ is other than amino or substituted amino, and 5' derivatives of such compounds including straight or branched chain alkyl esters optionally substituted with carboxy groups, (e.g. succinate), $C_{1-6}$ thio esters, optionally substituted aryl esters, mesylate, glucuronide or mono-, di- or tri-phosphates.

Further classes of preferred compounds of formula (II)B include those wherein
$R^6$ is amino, $C_{1-4}$ alkylamino, mercapto, hydroxy or $C_{1-4}$ alkoxy; and/or
$R^7$ is amino, $C_{1-4}$ alkylamino or hydrogen;
and 5' derivatives of such compounds including straight or branched chain alkyl esters optionally substituted with carboxy groups (e.g. succinate), $C_{1-6}$ thio esters, optionally substituted aryl esters, mesylate, glucuronide or mono-, di- or tri-phosphates.

Preferred compounds of formula (I) for use in the treatment or prophylaxis of viral infections are those compounds of formula (II) wherein
$R^1$ is hydroxy, mercapto, $C_{1-5}$ alkoxy, amino, $C_{6-12}$ aralkoxy or is an O-anhydro linkage connecting the 2 and 5' positions;
$R^2$ is hydrogen, methyl or benzoyl;
$R^3$ is hydroxy, mercapto, amino, substituted amino, $C_{6-12}$ aralkoxy or hydrogen.
$R^4$ is as defined, provided that A in formula (I) is not a thymine residue; and
pharmaceutically acceptable derivatives thereof. The azido group is advantageously in the erythro configuration. Particularly preferred are those compounds as described above which vary by only one of the substituents $R^1$-$R^4$ in the pyrimidine ring from those of a thymine residue (wherein $R^1$ and $R^3$ are hydroxy, $R^2$ is hydrogen and $R^4$ is methyl). Preferred compounds of formula (I) for use in the treatment or prophylaxis of viral infections are as described above for formula (I) but further include those compounds of formula (I)A wherein B is a thymine residue, and especially when the said compound is 3'-azido-3'-deoxythymidine.

Those compounds of formula (I) which are preferred for use in the treatment or prophylaxis of bacterial infections are those of formula (II) wherein:
$R^1$ is oxygen, sulphur, benzyloxy or methoxy;
$R^2$ is hydrogen or benzoyl;
$R^3$ is as defined above;
$R^4$ is methyl or halogen, provided that A in formula (I) is not a thymine residue; and pharmaceutically acceptable derivatives thereof.

The 3'-azido group may be in either configuration, but is particularly preferred in the erythro configuration, and preferred pharmaceutically acceptable derivatives are those 5' esters of simple organic acids, preferably $C_{1-18}$ acids.

Particularly preferred are those compounds as described above which vary by only one of the substituents $R^1$-$R^4$ in the pyrimidine ring from those of a thymine residue (wherein $R^1$ and $R^3$ are hydroxy, $R^2$ is hydrogen and $R^4$ is methyl).

Preferred compounds of formula (I)A for use in the treatment or prophylaxis of bacterial infections are as described above for formula (I) but further include those compounds of formula (I)A wherein B is thymine residue, and especially when the said compound is 3'-azido-3'-deoxythymidine.

By "a pharmaceutically acceptable derivative" is meant any pharmaceutically acceptable salt, ester, or salt of such ester, or any other compound which upon administration to the recipient, is capable of providing (directly or indirectly) the parent 3'-azidonucleoside or a therapeutically effective metabolite or residue thereof. An example of a non-ester compound is the derivative wherein the 5'-C- and 2-C-atoms are linked by an oxygen atom to form an anhydro group.

Preferred esters of the compounds of formula (I) include carboxylic acid esters in which the non-carbonyl moiety of the ester grouping is selected from straight or branched chain alkyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); and mono-, di- or triphosphate esters. Any reference to any of the above compounds also includes a reference to a pharmaceutically acceptable salt thereof.

With regard to the above-described esters, unless otherwise specified, any alkyl moiety present advantageously contains 1 to 18 carbon atoms, particularly 1 to 4 carbon atoms. Any aryl moiety present in such esters advantageously comprises a phenyl group.

Examples of pharmaceutically acceptable salts of the compounds of formula (I) and pharmaceutically acceptable derivatives thereof include base salts, e.g. derived from an appropriate base, such as alkali metal (e.g. sodium), alkaline earth metal (e.g. magnesium) salts, ammonium and $NX_4^+$ (wherein X is $C_{1-4}$ alkyl) and mineral acid salts, such as the hydrochloride.

Specific examples of pharmaceutically acceptable derivatives of the compound of formula (I) that may be used in accordance with the present invention include the monosodium salt and the following 5' esters: monophosphate; disodium monophosphate; diphosphate; triphosphate; acetate; 3-methyl-butyrate; octanoate; palmitate; 3-chloro benzoate; benzoate; 4-methyl benzoate; hydrogen succinate; pivalate; mesylate; propionate; hexanoate; methoxyacetate and phenoxyacetate.

Certain of the compounds according to the invention are new. Therefore, the present invention further provides the compounds of formula

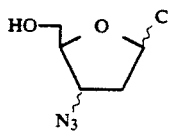

(I)B wherein
C is a purine or a pyrimidine base linked at the 9- or 1-position respectively, and pharmaceutically acceptable derivatives thereof, other than (a) compounds of formula (I)B wherein C is an adenine, guanine, uridine, cytidine or thymine base, and their 5'-mono- or 5'-triphosphate esters;

(b) the 5'-O-acetate 5'-O-trityl and 5'-O-(4-methylbenzenesulphonate) derivatives of the compound of formula (I)B wherein C is a uridine base and the 3'-azido group is in the erythro configuration;

(c) compounds of formula (I)B wherein C is (i) a 5-bromovinyluridine or 5-trifluoromethyluridine residue and the 3'-azido group is in the erythro configuration; (ii) a uridine residue and the 3'-azido group is in the threo configuration; and (iii) a 5-iodo or 5-fluorouridine residue and the 3'-azido group is in the erythro or threo configuration; and 5'-O-trityl derivatives of such compounds;

(d) compounds of formula (I)B wherein C is (i) a 5-bromovinyluridine or cytidine residue and the 3'-azido group is in the threo configuration; (ii) a 5-fluorocytidine residue and the 3'-azido group is in the erythro configuration; or (iii) a 5-methylcytidine residue and the 3'-azido group is in the threo or erythro configuration;

(e) the 5'-O-acetate esters of compounds of formula I(B) wherein C is a 4-chloro-2(1H)pyrimidinone or 4-(1H-1,2,4-triazol-1-yl)-2(1H)pyrimidinone (optionally substituted at the 5-position by fluorine or methyl) and the 3'-azido group is in erythro configuration;

(f) the 5'-O-[(4-methoxyphenyl)diphenylmethyl]-derivative of the compound of formula (I)B wherein C is a cytidine residue and the 3'-azido group is in the erythro configuration; and (g) the 5'-O-trityl derivative of the compound of formula (I)B wherein C is an adenine residue and the 3'-azido group is in the threo configuration.

Preferred compounds are those described above in association with therapy, other than those specifically excluded above.

The compounds of formulae (I) and (I)A, and their pharmaceutically acceptable derivatives, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose will be in the range of 3.0 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form. Experiments with 3'-azido-3'-deoxythymidine suggest that a dose should be administered to achieve peak plasma concentrations of the active compound of from about 1 to about 75 $\mu M$, preferably about 2 to 50 $\mu M$, most preferably about 3 to about 30 $\mu M$. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

The combinations according to the invention may be administered in a similar manner to that described above to provide the desired therapeutic dosages of the active ingredient and the further therapeutic agent concerned. The dosage of the combination will depend on the condition being treated, the particular active ingredient and the further therapeutic agent concerned and other clinical factors such as the weight and condition of the patient and the route of administration of the combination. As indicated above, the active ingredient and the further therapeutic agent may be administered simultaneously (e.g., in a unitary pharmaceutical formulation) or separately (e.g., in separate pharmaceutical formulations) and, in general, the combinations may be administered by the topical, oral, rectal or parenteral (e.g., intravenous, subcutaneous or intramuscular) routes.

In particular, combinations according to the invention wherein the second agent is a nucleoside transport inhibitor, may be administered to the subject concerned in conventional manner. However, for administration by the oral route a dosage of the active ingredient of 1 to 200 mg/kg/day, preferably 5 to 50 mg/kg/day, is generally sufficient. For administration by the parenteral route, a dosage of active ingredient of 1 to 100 mg/kg/day, preferably 2 to 30 mg/kg/day is generally sufficient. The amount of nucleoside transport inhibitor in the combination is independent of the amount of active ingredient specified above and is sufficient to inhibit nucleoside transport effectively and is preferably in the range of 0.1 to 100 mg/kg/day, and particularly in the range 1 to 20 mg/kg/day.

The combinations according to the invention, wherein the second agent is either a renal excretion inhibitor or a glucuronidation inhibitor or both, may be administered to the subject concerned in conventional manner. However, for administration by the oral route a dosage of active ingredient of 1 to 200 mg/kg/day, preferably 5 to 50 mg/kg/day, is generally sufficient. For administration by the parenteral route, a dosage of active ingredient of 1 to 100 mg/kg/day, preferably 2 to 30 mg/kg/day is generally sufficient. The amount of the renal excretion/glucuronidation inhibitor in the combination is independent of the amount of active ingredient and is sufficient in the range of 4–100 mg/kg/day, preferably 5–60 mg/kg/day, most preferably 10–40 mg/kg/day.

The combinations according to the invention, wherein the second agent is an interferon, beneficially comprise active ingredient at from 5 to 250 mg per kg per day; and the suitable effective dose range of interferon is $3 \times 10^6$ to $10 \times 10^6$ IU per square meter of body surface per day, preferably $4 \times 10^6$ to $6 \times 10^6$ IU per square meter per day. The active ingredient and interferon should be administered in the ratio of from about 5 mg per kg of active ingredient to $3 \times 10^6$ IU per square meter of interferon to about 250 mg per kg per day of active ingredient to $10 \times 10^6$ IU per square meter per day of interferon, preferably from about 5 mg per kg per day of active ingredient to $4 \times 10^6$ IU per square meter per day of interferon to about 100 mg per kg per day of active ingredient to $6 \times 10^6$ IU per square meter per day of interferon.

Interferon is preferably administered by injection (s.c., i.m. or i.v., for example), while the active ingredient is preferably administered orally or by injection, but may be administered by any mode described herein. Interferon and active ingredient may be administered together or separately, and the daily dose of each may preferably be administered as divided doses.

For combinations according to the invention wherein the second agent is another therapeutic nucleoside, a suitable effective oral dose range of active ingredient is 2.5 to 50 mg per kg of body weight per day, preferably 5 to 10 mg per kg per day; and the suitable effective oral dose range of the second therapeutic nucleoside is 5 to 100 mg per kg of body weight per day, preferably 15 to 75 mg per kg per day. It is preferred that the ratio for oral administration of active ingredient to the second therapeutic nucleoside should be in the range of about 1:1 to 1:10, more preferably from about 1:2 to 1:8.

The suitable effective i.v. dose range of active ingredient is generally about 1.5 to 15 mg per kg per day, and the suitable effective i.v. dose range of therapeutic nucleoside is generally about 5 to 30 mg per kg per day. It is preferred that the ratio for i.v. administration of active ingredient to the second therapeutic nucleoside should be in the range of about 2:1 to 1:20, more preferably from about 1:2 to 1:10.

Both components of the combination are preferably administered orally or by injection and may be given together or separately. The daily dose of each may be given as divided doses.

For combinations according to the invention wherein the second agent is an antibacterial agent, a suitable effective dose range of active ingredient is 2.5 to 50 mg/kg/day, preferably 5 to 10 mg/kg/day, and the suitable, effective dose range of the antibacterial agent is in the range of 2 to 1000 mg/kg/day, preferably 50 to 500 mg/kg/day. The preferred ratios of active ingredient to antibacterial agent are in the range of 20:1 to 1:500, particularly 2:1 to 1:125.

It will be appreciated that, while combinations containing three or more therapeutic agents are not specifically described herein, such combinations do form a part of the present invention. For example, a combination of 3'-azido-3'-deoxythymidine (AZT) with acyclovir and probenecid has the double advantage of both potentiating the activity of AZT and increasing its availability. Likewise, combinations of compounds of formula (I)A with two or more of the same variety of second therapeutic agent also form part of the invention, for example, AZT with sulfadimidine and Trimethoprim.

While it is possible for the active ingredient to be administered alone it is preferable to present it as a pharmaceutical formulation. The formulations of the present invention comprise at least one active ingredient, as above defined, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The compounds according to the invention may also be presented for use in the form of veterinary formulations, which may be prepared, for example, by methods that are conventional in the art. Examples of such veterinary formulations include those adapted for:

(a) oral administration, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

It will be appreciated that such formulations as are described above will also be suitable for the presentation of combinations according to the invention, whether unitary or separate formulations, and may be prepared in a like manner.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

The compounds of formula (I)A, and their pharmaceutically acceptable derivatives, may be prepared in conventional manner using techniques that are well known in the art, e.g. as described in: Synthetic Procedures in Nucleic Acid Chemistry (1, 321 (1968), T. A. Krenitsky et al), J. Med. Chem. (26, 981 (1983)); Nucleic Acid Chemistry, Improved and New Synthetic Processes, Methods and Techniques (Parts 1 and 2, Ed. L. D. Townsend, R. S. Tipson, (J. Wiley) 1978); J. R. Horwitz et al. (J. Org. Chem. 29, (July 1964) 2076–78); M. Imazawa et al. (J. Org. Chem, 43 (15) (1978) 3044–3048); K. A. Watanabe et al. (J. Org. Chem., 45, 3274 (1980)); and R. P. Glinski et al. (J. Chem., Soc. Chem. Commun., 915 (1970)), which disclosures are herein incorporated by reference, or using techniques that are analogous to those described therein.

The present invention further includes a process for the preparation of a compound of formula (I) and pharmaceutically acceptable derivatives thereof which comprises reacting a compound of formula:

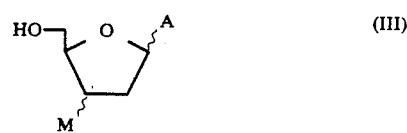

(wherein A is as defined above and M represents a precursor group for the 3'-azido group) or a derivative (e.g. an ester or salt) thereof, with an agent or under conditions serving to convert the said precursor group into the desired azido group;

(B) reacting a compound of formula.

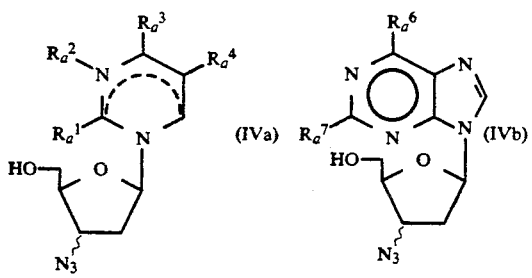

(wherein $R_a^1$, $R_a^2$, $R_a^3$, $R_a^4$, $R_a^6$ and $R_a^7$ respectively represent the groups $R^1$, $R^2$, $R^3$ $R^4$, $R^6$ and $R^7$ or precursor groups therefor, providing that at least one of $R_a^1$, $R_a^2$, $R_a^3$ and $R_a^4$ in formula (IV a) or at least one of the groups $R_a^6$ and $R_a^7$ in formula (IV b) represents a precursor group) with an agent or under conditions serving to convert the said precursor group(s) into the corresponding desired groups;

(C) reacting a compound of formula

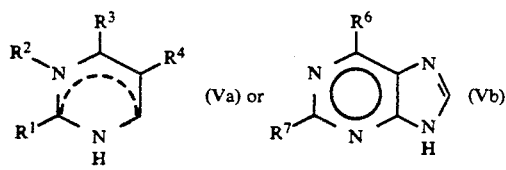

(wherein $R^1$, $R^2$, $R^3$, $R^4$, $R^6$ and $R^7$ are as defined above) or a functional equivalent thereof, with a compound serving to introduce the desired ribofuranosyl ring at the 1-position of the compound of formula (IVa) or the 9-position of formula (IVb); or (D) for the preparation of compounds of formula (II) reacting a purine of formula (V b) with a pyrimidine nucleus of formula

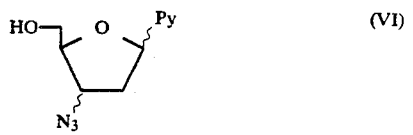

(wherein Py represents a 1-pyrimidinyl group); and thereafter, or simultaneously therewith, effecting one or more of the following optional conversions:

(i) when a compound of formula (I) is formed, converting the said compound into a pharmaceutically acceptable derivative thereof; and (ii) when a pharmaceutically acceptable derivative of a compound of formula (I) is formed, converting the said derivative into the parent compound of formula (I) or into an alternative pharmaceutically acceptable derivative of a compound of formula (I).

In the above-described process according to the invention, it will be appreciated that the choice of the precursor compounds in processes (A) to (D) will be dictated largely by the particular compound that it is desired to prepare, the above-mentioned agents and conditions being selected accordingly from those that are known in the art of nucleoside synthetic chemistry. Examples of such conversion procedures are described hereinafter for guidance and it will be understood that they can be modified in conventional manner depending on the desired compound. In particular, for example, where a conversion is described which would otherwise result in the undesired reaction of labile groups then such groups may be protected in conventional manner, with subsequent removal of the protecting groups after completion of the conversion.

Thus, for example, with regard to process (A) the group M in the compound of formula (IIIa) or (IIIb) may represent, for example, a halogen (e.g. chlorine) hydroxy or organosulphonyloxy (e.g. trifluoromethylsulphonyloxy, methanesulphonyloxy or p-toluene sulphonyloxy) radical.

For the preparation of compounds of formula (I) in which the 3'-azido group is in the threo configuration, a compound of formula (IIIa) or (IIIb) in which the group M is a hydroxy group in the erythro configuration (in which the 5'-hydroxy group is advantageously protected e.g. with a trityl group) may be treated for example with triphenylphosphine, carbon tetrabromide and lithium azide. Alternatively M may represent an organosulphonyloxy leaving-group in the erythro configuration which may be converted into an azido group in the threo configuration by treatment, for example, with lithium or sodium azide, the 5'-hydroxy group being similarly protected as described above. Removal of the 5'-trityl protecting group may be subsequently effected, e.g. by treatment under mild acidic conditions or zinc bromide.

For the preparation of compounds of formula (I) in which the 3'-azido group is in the erythro configuration, a compound of formula (IIIa) or (IIIb) in which the group M is a halogen (e.g. chloro) group in the threo configuration (in which the 5'-hydroxy is advantageously protected, e.g. with a trityl group) may be treated for example with lithium or sodium azide. The 3'-threo-halogen (e.g. chlorine) starting material may be obtained, for example, by reaction of the corresponding 3'-erythro-hydroxy compound with, for example, triphenylphosphine and carbon tetrachloride, or alternatively by treatment with organosulphonyl halide (e.g. trifluoromethanesulphonyl chloride) to form a corresponding 3'-erythro-organosulphonyloxy compound which is then halogenated e.g. as described above. Alternatively a 3'-threo-hydroxy or organosulphonyloxy compound of formula (IIIa) or (IIIb) may be treated, for example with triphenylphosphine, carbon tetrabromide and lithium azide to form the corresponding 3'-erythro azido compound.

With regard to process (B) the following represent examples of various procedures by which the precursor groups in formula (IVa) may be converted into the desired $R^1$, $R^2$, $R^3$ and $R^4$ groups:

a) When $R^1$ represents an alkoxy (e.g. methoxy or ethoxy) group, such compounds may be prepared from corresponding compounds of formula (IVa) in which $R_a^1$ represents a 2,5'-O-anhydro linkage e.g. by treatment with an appropriate nucleophile e.g. an alkoxide, conveniently in the presence of potassium carbonate;

b) When $R^1$ represents a mercapto group, such compounds may be prepared from corresponding compounds of formula (IVa) in which $R_a^1$ represents an alkoxy (e.g. ethoxy) group, e.g. by treatment with hydrogen sulphide;

c) When $R^2$ represents an alkyl group, such compounds may be prepared from corresponding compounds of formula (IVa) in which $R_a^2$ represents a hydrogen atom, e.g. by treatment with an alkylating agent, e.g. N,N-dimethylformamide dimethylacetal;

d) When $R^3$ represents a mercapto group, such compounds may be prepared from corresponding compounds of formula (IVa) in which $R_a^3$ represents an appropriate leaving group, e.g. 1,2,4-triazolyl, by treatment for example with an alkali metal (e.g. sodium) mercaptan;

e) When $R^3$ represents an amino group, such compounds may be prepared from corresponding compounds of formula (IVa) in which $R_a^3$ represents a hydroxy group by treatment with an aminating agent, e.g. hexamethyl disilazane and ammonium sulphate, in a bomb;

f) When $R^4$ represents a halo (e.g. chloro) radical, such compounds may be prepared from corresponding compounds of formula (IVa) in which $R_a^4$ represents a hydrogen atom by treatment with a halogenating agent e.g. m-chloroperbenzoic acid.

Similar procedures may be used to effect conversion of the precursor group in formula (IVb) into the desired $R^6$ and $R^7$ group, as well as procedures described for example in the above-mentioned references.

With regard to process (C), this may be effected for example by treating the appropriate pyrimidine or purine of formula (Va) or (Vb) or a salt or protected derivative thereof, with a compound of formula

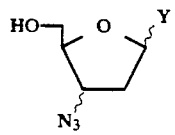

(wherein Y represents a leaving group, e.g. an acetoxy or benzoyloxy or halo, e.g. chloro group and the 5' hydroxyl group is optionally protected e.g. by a p-toluenesulphonyloxy group), and subsequently removing any protecting groups.

With regard to process (D) the reaction of the compounds of formulae (Vb) and (VI) is conviently effected in the presence of a phosphorylating enzyme, and if desired, separation of the 3'-azido anomers in conventional manner.

Where a compound of formula (I) is formed, such a compound may be converted into a pharmaceutically acceptable phosphate or other ester by reacting the compound of formula (I) with respectively a phosphorylating agent, e.g. $POCl_3$ or an appropriate esterifying agent, e.g. an acid halide or anhydride. The compounds of formula (I), including esters thereof, may be converted into pharmaceutically acceptable salts thereof in conventional manner, e.g. by treatment with an appropriate base.

Where a derivative of a compound of formula (I) is formed, such a compound may be converted into the parent compound e.g. by hydrolysis.

The following Examples are intended for illustration only and are not intended to limit the scope of the invention in any way. The term 'active ingredient' as used in the Examples means a compound of formula (I) or (I)A or a pharmaceutically acceptable derivative thereof.

EXAMPLE 1

Tablet Formulations

The following formulations A and B are prepared by wet granulation of the ingredients with a solution of povidone, followed by addition of magnesium stearate and compression.

|  | mg/tablet | mg/tablet |
|---|---|---|
| Formulation A | | |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |
| Formulation B | | |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |
| Formulation C | | |
| Active ingredient | 100 | |
| Lactose | 200 | |
| Starch | 50 | |
| Povidone | 5 | |
| Magnesium stearate | 4 | |
| | 359 | |

The following formulations, D and E, are prepared by direct compression of the admixed ingredients. The lactose used in formulation E is of the direct compression type (Dairy Crest—"Zeparox").

|  | mg/capsule |
|---|---|
| Formulation D | |
| Active Ingredient | 250 |
| Pregelatinised Starch NF 15 | 150 |
| | 400 |
| Formulation E | |
| Active Ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

|  |  | mg/tablet |
|---|---|---|
| (a) | Active Ingredient | 500 |
| (b) | Hydroxypropylmethylcellulose (Methocel K4M Premium) | 112 |
| (c) | Lactose B.P. | 53 |
| (d) | Povidone B.P.C. | 28 |
| (e) | Magnesium Stearate | 7 |
|  |  | 700 |

EXAMPLE 2

Capsule Formulations

Formulation A

A capsule formulation is prepared by admixing the ingredients of Formulation D in Example 1 above and filling into a two-part hard gelatin capsule. Formulation B (infra) is prepared in a similar manner.

| | mg/capsule |
|---|---|
| Formulation B | |
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active ingredient | 250 |
| (b) Macrogol 4000 BP | 350 |
| | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

EXAMPLE 3

Injectable Formulation

| Formulation A. | | |
|---|---|---|
| Active ingredient | | 0.200 g |
| Hydrochloric acid solution, 0.1 M | q.s. to pH | 4.0 to 7.0 |
| Sodium hydroxide solution, 0.1 M | q.s. to pH | 4.0 to 7.0 |
| Sterile water | q.s. to | 10 ml |

The active ingredient is dissolved in most of the water (35°–40° C.) and the pH adjusted to between 4.0 and 7.0 with the hydrochloric acid or the sodium hydroxide as appropriate. The batch was then made up to volume with the water and filtered through a sterile micropore filter into a sterile 10 ml amber glass vial (type 1) and sealed with sterile closures and overseals.

| Formulation B. | |
|---|---|
| Active ingredient | 0.125 g |
| Sterile, pyrogen-free, pH 7 phosphate buffer, q.s. to | 25 ml |

EXAMPLE 4

Intramuscular Injection

| | Weight (g) |
|---|---|
| Active ingredient | 0.20 |
| Benzyl Alcohol | 0.10 |
| Glycofurol 75 | 1.45 |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 5

Syrup

| Formulation A | Weight (g) |
|---|---|
| Active ingredient | 0.2500 |
| Sorbitol Solution | 1.5000 |
| Glycerol | 2.0000 |
| Sodium Benzoate | 0.0050 |
| Flavour, Peach 17.42.3169 | 0.0125 ml |
| Purified Water q.s. to | 5.0000 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

When the active ingredient is poorly soluble, the following formulation (B) is used.

| Formulation B. | Weight (g) |
|---|---|
| Active Ingredient | 0.250 |
| Sorbitol Solution | 1.500 |
| Glycerol | 0.005 |
| Dispersible Cellulose | 0.005 |
| Sodium Benzoate | 0.010 ml |
| Flavour | |
| Purified Water to | 5.000 ml |

Mix the sorbitol solution, glycerol and part of the purified water. Dissolve the sodium benzoate in purified water and add the solution to the bulk. Add and disperse the dispersible cellulose and flavour. Add and disperse the active ingredient. Make up to volume with purified water.

EXAMPLE 6

Suppository

| | mg/suppository |
|---|---|
| Active Ingredient (63 μm)* | 250 |
| Hard Fat, BP (Witepsol H15 - Dynamit NoBel) | 1770 |
| | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stired to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic moulds. The suppositories are allowed to cool to room temperature.

EXAMPLE 7

Pessaries

|  | mg/pessary |
|---|---|
| Active ingredient (63 μm) | 250 |
| Anhydrous Dextrose | 380 |
| Potato Starch | 363 |
| Magnesium Stearate | 7 |
|  | 1000 |

The above ingredients are mixed directly and pessaries prepared by direct compression of the resulting mixture.

The following examples 8-10 illustrate the preparation of formulations containing a compound of formula (I)A (active ingredient) and a further therapeutic nucleoside as specified.

EXAMPLE 8

Injection

|  | Weight (mg) |
|---|---|
| Formulation A. | |
| Acyclovir | 400 |
| Active Ingredient | 200 |
| 1M NaOH | as required |
| Sterile Water to | 10 ml |
| Formulation B | |
| 2-Amino-9-(2-hydroxyethoxymethyl)purine | 400 |
| Active Ingredient | 200 |
| 1M NaOH | as required |
| Sterile Water to | 10 ml |

For the above formulations the therapeutic nucleoside is added to 1M NaOH solution and stirred until dissolved. The active ingredient is added and dissolved. Add sterile water to 10 ml. Filter through a sterile filter and fill into sterile vials. Freeze dry.

EXAMPLE 9

Tablets

|  | Weight (mg) |
|---|---|
| Formulation A. | |
| Acyclovir | 500 |
| Active Ingredient | 125 |
| Povidone | 14 |
| Sodium Starch Glycollate | 25 |
| Magnesium Stearate | 6 |
|  | 670 |
| Formulation B. | |
| Active Ingredient | 125 |
| 2-Amino-9-(2-hydroxyethoxymethyl)purine | 125 |
| Povidone | 8 |
| Sodium Starch Glycollate | 12 |
| Magnesium Stearate | 3 |
|  | 273 |

For the above formulations A and B, the therapeutic nucleoside and active ingredient are mixed with the sodium starch glycollate and granulated with a solution of povidone. After drying, the granules are blended with magnesium stearate and compressed.

EXAMPLE 10

Capsules

| Formulation A. | Weight (mg) |
|---|---|
| Acyclovir | 250 |
| Active Ingredient | 62.5 |
| Lactose | 170.5 |
| Sodium Starch Glycollate | 15 |
| Magnesium Stearate | 2 |
|  | 500 |

Mix the ingredients and fill into hard gelatin capsules.

| Formulation B. | Weight (mg) |
|---|---|
| Active Ingredient | 125 |
| 2-Amino-9-(2-hydroxyethoxymethyl)purine | 125 |
| Lactose | 133 |
| Sodium Starch Glycollate | 15 |
| Magnesium Stearate | 2 |
|  | 400 |

Mix the ingredients and fill into hard gelatin capsules.

Example 11 illustrates a formulation containing interferon and a compound of formula (I)A (active ingredient).

EXAMPLE 11

Injection

| Interferon | 3 Mega Units |
|---|---|
| Active Ingredient | 200 mg |
| Sterile Buffer pH 7 to | 50 ml |

Dissolve the interferon and active ingredient in the sterile water. Filter through a sterile filter and fill into sterile vials.

The following Examples 12-15 describe the preparation of formulations containing a compound of formula I(A) (the Active Ingredient), for example 3'-azido-3'-deoxythymidine, in combination with a nucleoside transport inhibitor e.g. dipyridamole.

EXAMPLE 12

Tablet

|  | Weight (mg) |
|---|---|
| Nucleoside transport inhibitor | 300 |
| Active Ingredient | 200 |
| Lactose | 105 |
| Starch | 50 |
| Polyvinylpyrrolidinone | 20 |
| Magnesium stearate | 10 |
| Total Weight | 685 |

The active compounds are mixed with the lactose and starch and wet granulated with a solution of the polyvinylpyrrolidinone. The granules are dried, sifted, and blended with magnesium stearate and then compressed into tablet form.

EXAMPLE 13

Capsule

|  | Weight (mg) |
|---|---|
| Nucleoside transport inhibitor | 300 |
| Active Ingredient | 100 |
| Lactose | 100 |
| Sodium starch glycollate | 10 |
| Polyvinylpyrrolidinone | 10 |
| Magnesium stearate | 3 |
| Total Weight | 523 |

The active compounds are mixed with the lactose and sodium starch glycollate and wet granulated with a solution of the polyvinylpyrrolidinone. The granules are dried, sifted and blended with the magnesium stearate and filled into hard gelatin capsules.

EXAMPLE 14

Cream

|  | Weight (g) |
|---|---|
| Nucleoside transport inhibitor | 7.5 |
| Active Ingredient | 5.00 |
| Glycerol | 2.00 |
| Cetostearyl alcohol | 6.75 |
| Sodium lauryl sulphate | 0.75 |
| White soft paraffin | 12.50 |
| Liquid paraffin | 5.00 |
| Chlorocresol | 0.10 |
| Purified Water to | 100.00 |

The active compounds are dissolved in a mixture of purified water and glycerol and heated to 70° C. The remaining ingredients are heated together at 70° C. The two parts are added together and emulsified. The mixture is cooled and filled into containers.

EXAMPLE 15

Intravenous Injections

|  |  | Amount (mg) |
|---|---|---|
| (1) | Active Ingredient | 200 |
|  | Nucleoside transport inhibitor | 300 |
|  | Glycerol | 200 |
|  | Sodium hydroxide solution qs | pH 7.0–7.5 |
|  | Water for Injections to | 10 ml |

The glycerol is added to some of the water for Injections. The two active compounds are added and the pH adjusted to 7.0–7.5 with sodium hydroxide solution. The solution is made up to volume with additional Water for Injections. Under aseptic conditions, the solution is sterilized by filtration, filled into sterile ampoules and the ampoules sealed.

|  |  | Amount (mg) |
|---|---|---|
| (2) | Active Ingredient | 100 |
|  | Nucleoside transport inhibitor | 150 |
|  | Mannitol | 125 |
|  | Sodium hydroxide solution qs to | pH 8.0–9.0 |
|  | Water for Injections to | 2.5 ml |

The active compounds and the mannitol are dissolved in a part of the water for injections. The pH is adjusted to 8.0–9.0 with the sodium hydroxide solution and made up to volume with additional water for injections. Under aseptic conditions, the solution is sterilized by filtration, filled into sterile vials and the water removed by freeze-drying. The vials are sealed under an atmosphere of nitrogen and closed with a sterile closure and metal collar.

The following examples 16–18 describe the preparation of formulations containing a compound of formula I(A) (the Active Ingredient), for example 3'-azido-3'-deoxythymidine, in combination with a glucuronidation/renal excretion inhibitor, for example probenecid.

EXAMPLE 16

Tablet

|  | Weight (mg) |
|---|---|
| Active Ingredient | 100 |
| Glucuronidation/renal excretion inhibitor | 200 |
| Lactose | 105 |
| Starch | 50 |
| Polyvinylpyrrolidinone | 20 |
| Magnesium stearate | 10 |
| Total Weight | 485 |

The active compounds are mixed with the lactose and starch and wet granulated with a solution of the polyvinylpyrrolidinone. The granules are dried, sifted, and blended with magnesium stearate and then compressed into tablet form.

EXAMPLE 17

Capsule

|  | Weight (mg) |
|---|---|
| Active Ingredient | 100 |
| Glucuronidation/renal excretion inhibitor | 100 |
| Lactose | 100 |
| Sodium starch glycollate | 10 |
| Polyvinylpyrrolidinone | 10 |
| Magnesium stearate | 3 |
| Total Weight | 323 |

The active compounds are mixed with the lactose and sodium starch glycollate and wet granulated with a solution of the polyvinylpyrrolidinone. The granules are dried, sifted and blended with the magnesium stearate and filled into hard gelatin capsules.

EXAMPLE 18

Intravenous Injections

|  |  | Amount (mg) |
|---|---|---|
| (1) | Active Ingredient | 200 |
|  | Glucuronidation/renal excretion inhibitor | 300 |
|  | Glycerol | 200 |
|  | Sodium hydroxide solution qs | pH 7.2–7.5 |
|  | Water for Injections to | 10 ml |

The glycerol is added to some of the water for injections. The two active compounds are added and the pH adjusted to 7.0–7.5 with sodium hydroxide solution. The solution is made up to volume with additional water for injections. Under aseptic conditions, the solution is sterilized by filtration, filled into sterile ampoules and the ampoules sealed.

|                                          | Amount (mg) |
|------------------------------------------|-------------|
| (2) Active Ingredient                    | 100         |
| Glucuronidation/renal excretion inhibitor| 150         |
| Mannitol                                 | 125         |
| Sodium hydroxide solution qs to          | pH 8.0–9.0  |
| Water for Injections to                  | 2.5 ml      |

The active compounds and the mannitol are dissolved in a part of the water for injections. The pH is adjusted to 8.0–9.0 with the sodium hydroxide solution and made up to volume with additional water for injections. Under aseptic conditions, the solution is sterilized by filtration, filled into sterile vials and the water removed by freeze-drying. The vials are sealed uner an atmosphere of nitrogen and closed with a sterile closure and metal collar.

Veterinary Formulations (Examples 19–22)

EXAMPLE 19

Tablet for Small Animal Use

|                          | Per tablet |
|--------------------------|------------|
| Active Ingredient        | 120 mg     |
| Maize Starch             | 20.0 mg    |
| Microcrystalline Cellulose | 100.0 mg |
| Magnesium Stearate       | 1.5 mg     |

The active ingredient, microcrystalline cellulose and maize starch are mixed together. Sufficient starch solution is added with continued mixing to produce a moist mass, which is passed through a sieve to produce granules. The magnesium stearate is sifted on. Tablets are produced by direct compression of the granules.

EXAMPLE 20

Granules for In-Feed Medication

|                          | Weight (g) |
|--------------------------|------------|
| Active ingredient        | 6.0        |
| Povidone                 | 1.0        |
| Lactose                  | 93.0       |
| Aqueous alcohol mixture qs. |         |

The active ingredient is mixed with the lactose. To this is added the aqueous alcohol containing the dissolved povidone. Sufficient aqueous alcohol is added to produce a moist mass, which is passed through a sieve to produce granules which are subsequently dried.

EXAMPLE 21

Oral Paste

|                          | Weight (g) |
|--------------------------|------------|
| Active ingredient        | 24         |
| Xanthan Gum              | 0.5        |
| Methyl Hydroxybenzoate   | 0.1        |
| Polysorbate 80           | 0.1        |
| Purified Water to        | 100.0 ml   |

The polysorbate 80 and methyl hydroxybenzoate are dissolved in the bulk of the water. The xanthan gum is added and dispersed and allowed to swell. The active ingredient is added and dispersed and diluted to volume.

EXAMPLE 22

Ointment

|                     | Weight (g) |
|---------------------|------------|
| Active ingredient   | 12         |
| White Soft Paraffin | 88.0       |

The white soft paraffin is melted at 60° C. The active ingredient is added and dispersed, allowed to cool, and filled into collapsible metal tubes.

EXAMPLE 23

3'-Azido-3',5'-dideoxy-5'-[(N,N-Dimethylthiocarbamoyl)thio]thymidine (a) The 5'-hydroxyl group of 3'-azido-3'-deoxythymidine (3.0 g, 11.2 mMol) was mesylated by the addition of methanesulphonyl chloride (2.7 mL) to a solution of the 3'-azido-3'-deoxythymidine in dry pyridine (20 mL). The reaction was allowed to proceed at 5° C. for one hour, then poured onto ice water. The precipitate was collected by filtration. The desired product was obtained by reacting the 3'-azido-3'-deoxy-5'-mesylthymidine obtained from the first step with potassium carbonate (0.78 g, 5.6 mMol) in DMF (75 mL). The reaction was heated in an 80° C. oil bath for six hours, then poured into ice water. The product was extracted from the water with ethyl acetate. The solvent was removed in vacuo and the resultant oil was flash chromatographed on silica gel by elution with $CHCl_3$:MeOH (9:1 v/v). The product was obtained in low yield. mp=184°–186° C.

(b) The sodium salt of dimethyldithiocarbamic acid dihydrate (0.642 g, 3.58 mMol) and 3.58 mL of a solution of 1N tetrabutylammonium hydroxide in MeOH was added to 25 mL of DMF. The solution was boiled to remove water and MeOH. After cooling, 2,5'-O-anhydro-3'-azido-3'-deoxythymidine (0.85 g, 3.4 mMol) dissolved in 15 mL of DMF was added. The reaction was heated in a 55° C. oil bath overnight. The reaction was poured onto ice water and a precipitate was removed by filtration. The product was extracted from the filtrate with ethyl acetate. The ethyl acetate was removed in vacuo and the resulting oil was purified by flash chromatography on silica gel by elution with $CHCl_3$:MeOH (95:5 v/v). Chromatography was required a second time on silica gel. The second elution was with $CHCl_3$:MeOH (98:2 v/v). Final purification was accomplished by reverse phase chromatography on $C_{18}$ eluted with water:methanol (3:7). The yield was 2.5%.

EXAMPLE 24

3'-Azido-3'-deoxy-5'-O-acetyl-4-thiothymidine

3'-Azido-3'-deoxy-5'-O-acetyl-4-(1,2,4-triazole)-thymidine (Lin, et al., ,J. Med. Chem. 26, 1691 (1983)) (1.41 g; 3.9 mMol) was dissolved in 100 mL acetone and 30 mL $H_2O$, then treated with 0.39 g $NaSH.xH_2O$ (Sung, J. Chem. Soc. Chem. Comm. 522, (1982)). The mixture was stirred for 30 min, the volume reduced by ½ and extracted with 200 mL $CHCl_3$. The $CHCl_3$ was washed with 100 mL $H_2O$ and dried over $Na_2SO_4$. The solvent was removed in vacuo and the resultant oil placed on a silica gel pad (6.5×3 cm) followed by elution with 750 mL $CHCl_3$. The solvent was removed in vacuo to yield a yellow oil which was recrystallized from i-PrOH to yield 0.64 g. (1.9 mMol; 48.7%); mp=75°–78° C.

EXAMPLE 25

3'-Azido-3'-deoxy-4-thiothymidine

3'-Azido-3'-deoxy-5'-O-acetyl-4-thiothymidine (0.25 g; 0.76 mMol, Example 21) was dissolved in a mixture of 5 mL of dioxane and 5 mL of conc. NH$_4$OH and stirred for 18 hrs. The solvent was removed in vacuo and the residue applied to a silica gel column followed by elution with CHCl$_3$/EtOAc (3:1 v/v). The appropriate fractions were combined and the solvent removed in vacuo to yield a yellow oil which was dissolved in Et$_2$O, forming crystals upon concentration: 0.16 g (0.56 mMol; 74%); m.p.=116°–118° C.

EXAMPLE 26

3-N-Methyl-3'-azido-3'-deoxythymidine

3'-Azido-3'-deoxythymidine (0.5 g; 1.9 mMol) and N,N-dimethylformamide dimethylacetal (Zemlicka, Coll. Czech. Chem. Comm. 35, 3572 (1972)) (0.9 mL; 7.5 mMol) were refluxed in 20 mL CHCl$_3$ for 48 hours. The solvent was removed in vacuo and the material placed on a silica solumn. Elution with EtOAc/CHCl$_3$ (1:1 v/v) resulted in pure material as a viscous oil: 0.26 g (0.9 mMol, 47%).

EXAMPLE 27

3'-Azido-3'-deoxy-2-thiothymidine

The synthesis of 3'-Azido-2-thiothymidine was accomplished by a five step reaction sequence starting from 2,3'-O-anhydro-5'-tritylthymidine (J. J. Fox, J. Org. Chem, 28, 936, (1963)).

2,3'-O-Anhydro-5'-tritylthymidine (10.5 g, 22.4 mMol) was added to a solution of sodium (0.52 g, 22.4 mMol) in dry ethanol (1.2 L) and the reaction was refluxed for six hours. The reaction was cooled and neutralized with 1N HCl. The solvent was removed in vacuo and the resultant oil purified by flash chromatography on silica gel by elution with CHCl$_3$:MeOH (96:4 v/v). A 30% yield of 1-(2'-deoxy-5'-trityl-D-lyxofuranosyl)-2-ethoxythymine was obtained. The 2-ethoxythymidine derivative (3.5 g, 16.8 mMol) was dissolved in 35 mL of DMF containing 2.2 mL of triethylamine. The cold solution was saturated with H$_2$S. The reaction was placed in a steel bomb and heated at 95° C. After twenty seven hours TLC indicated that no starting material remained. The reaction was purged with N$_2$ for several hours and poured onto ice water. The product was collected by filtration and purified by flash chromatography on silica gel by elution with CHCl$_3$:MeOH (97:3 v/v). A 37% yield of 1-(2'-deoxy-5'-trityl-β-D-lyxofuranosyl)-2-thiothymine was obtained. The UV max at pH1 of 277 nm and at pH11 of 241 nm indicated the formation of a 2-thiothymidine.

The 3'-hydroxyl group of the thiothymidine derivative was mesylated as follows: methanesulphonyl chloride (665 mL, 3.5 eq.) was added in four portions over six hours to a solution of 1-(2'-deoxy-5'-trityl-β-D-lyxofuranosyl)-2-thiothymidine (1.25 g) in dry pyridine (15 mL) at 5° C. The reaction was maintained at 5° C. overnight. The reaction was poured onto ice water and the product collected by filtration. Purification was accomplished by flash chromatography on silica gel by elution with ethylacetate:hexane (1:1 v/v). The yield was 50%.

Lithium azide (0.3 g, 6 mMol) was dissolved in 20 mL of dry DMF and 1-(2'-deoxy-3'-mesyl-5'-trityl-β-D-lyxofuranosyl)-2-thiothymine (0.72 g, 1.2 mMol) was added. The DMF solution was heated at 85° C. for 2.5 hours. The reaction was poured onto ice water and the product collected by filtration. Purification was accomplished by flash chromatography on silica gel by elution with CHCl$_3$:MeOH (98:2 v/v). The yield was 78%. A band in the IR at 2100 CM$^{-1}$ indicated the presence of an alkyl azide. The UV confirmed the presence of a 2-thiothymidine.

The final product was prepared by deblocking the 5'-hydroxyl group of 3'-azido-3'-deoxy-2-thio-5'-tritylthymidine (0.1 g) in 80% acetic acid (5 mL) on a steambath for 45 minutes. 3'-Azido-3'-deoxy-2-thiothymidine (0.021 g) was obtained by chromatography on silica gel by elution with CHCl$_3$:MeOH (96:4 v/v) in 37% yield.

EXAMPLE 28

3'-Azido-3'-deoxy-2-ethoxythymidine

3'-Azido-3'-deoxy-2-ethoxythymidine was prepared by refluxing 3'-azido-3'-deoxy-5'-mesylthymidine (2.6 g, 7.5 mMol) in dry ethanol (25 mL) with two equivalents of potassium carbonate (1.08 g, 7.5 mMol) for five hours. The solution was neutralized and taken to an oil in vacuo. The oil was purified by flash chromatography on silica gel by elution with ethyl acetate:methanol. The desired product was isolated in 39% yield; mp=98°–100° C.

EXAMPLE 29

3'-Azido-3'-deoxy-2-methoxythymidine

3'-Azido-3'-deoxy-2-methoxythymidine was prepared from 3'-azido-3'-deoxy-5'-mesylthymidine (1.6 g, 4.6 mMol) by the procedure of Example 25. The yield was 42%.; mp=47°–51° C.

EXAMPLE 30

3'-Azido-2',3'-dideoxy-5-methylisocytidine 2,5'-O-Anhydro-3'-azido-3'-deoxythymidine (0.35 g; 1.4 mMol) was dissolved in 15 mL of MeOH presaturated with ammonia and placed in a bomb at 77° C. (oil bath) for 48 hours (Skaric and Matulic-Adamic, Helv. Chim. Acta. 63, 2179 (1980)). By TLC (6:1 v/v CHCl$_3$/MeOH) the reaction was incomplete. The solvent was removed in vacuo and the resultant oil placed on a silica gel column followed by elution with CHCl$_3$/MeOH (6:1 v/v). The appropriate fractions were combined to yield 0.14 g (0.53 mMol; 38%) of the title compound; mp=107°–108° C.

EXAMPLE 31

3'-Azido-5-chloro-2',3'-dideoxyuridine

3'-Azido-2',3'-dideoxyuridine (0.25 g; 1 mMol) was dissolved in 2 mL dry dimethylacetamide (DMAC), cooled to 0° C. and 2 mL of 0.5M HCl in DMAC was added. m-Chloroperbenzoic acid (0.277 g; 1.6 mMol) was added in two portions over ten minutes and the mixture was allowed to come to ambient temperature. After two hours, 4 mL H$_2$O was added and the solution filtered. The aqueous DMAC solution was extracted with Et$_2$O (3×3 mL) and the Et$_2$O was evaporated in vacuo to an oil which was applied to a silica gel column. Elution with CHCl$_3$MeOH (15:1 v/v), combination of the appropriate fractions and evaporation in vacuo yielded an oil which was crystallized from Et$_2$O to give 58.5 mg (0.2 mMol, 20%): mp=169°–170° C.

UV (nm): at pH1 λmax=276 (ε=7400), λmin=239(ε=500); at pH 13 λmax=274 (ε=6400), λmin=249 (ε=3800).

$H^1$NMR (DMSO-$d_6$) δ8.29 (s,1H,H6), 6.04 (t,1H,H1', J=5.5 Hz), 5.49-5.29 (m, 1H,5'-OH), 4.44-4.20 (m,1H,H3'), 3.88-3.71 (m, 1H,H4'), 3.71-3.53 (m,2H,H5'), 2.63-2.31 (m,2H,H2'); Analysis for $C_9H_{10}N_5O_4Cl$ Calculated: C 37.58, H 3.50, N, 24.35, Cl 12.32. Found: C 37.67, H 3.54, N 24.39, Cl 12.40.

EXAMPLE 32

3'-Azido-5-bromo-2',3'-dideoxyuridine

3'-Azido-5-bromo-2',3'-dideoxyuridine was prepared from the known 3'-azido-2',3'-dideoxyuridine (T. A. Krenitsky, et al., J. Med. Chem., 26, 891, (1983)) (0.827 g, 3.3 mMol) by first acetylating the 5'-hydroxyl group with acetic anhydride (15 mL) then by brominating the 5 position by the addition of acetic acid (0.5 mL) and bromine (0.566 g). The red-brown solution was stirred at room temperature for two hours. The reaction was taken to an oil in vacuo and triturated with ethyl ether. The oil was dissolved in methanol ammonia to remove the acetyl group. The desired product was isolated by chromatography on silica gel by elution with CHCl$_3$:MeOH (95:5 v/v). The yield was 32%; mp=148°-149° C.

EXAMPLE 33

3'-Azido-2',3'-dideoxy-5-iodouridine

3'-Azido-2',3'-dideoxy-5-iodouridine was prepared from 2',3'-dideoxy-5-iodouridine (10 g, 28 mmol) by a four step reaction sequence described in the literature (T. A. Krenitsky, et al., J. Med. Chem., 26, 891, (1983)); mp=126°-130° C.

EXAMPLE 34

3'-Azido-2',3'-dideoxy-5-trifluoromethyluridine

3'-Azido-2',3'-dideoxy-5-trifluoromethyluridine was prepared by the following four step reaction sequence.

The 5'-hydroxyl group of 2',3'-dideoxy-5-trifluoromethyluridine (5.0 g, 16.9 mMol) was tritylated by the addition of triphenylmethyl choride (5.65 g, 20.3 mMol) to the starting material in a suspension of dichloromethane (1.4 L ml), pyridine (70 mL), and 3 A molecular sieves (55 g). The reaction was stirred at room temperature for four days. After filtration and evaporation in vacuo, the oily product was chromatographed on silica gel by elution with CH$_2$Cl$_2$:MeOH (95:5 v/v). The product fractions were combined and the solvent removed in vacuo. The resulting oil was triturated with water and the solid that formed was collected by filtration. The 3'-hydroxyl was chlorinated by dissolving the 5'-protected uridine (3.0 g) in dimethylacetamide (30 mL) containing triphenylphosphine (3.27 g) and adding carbon tetrachloride (51 mL). The reaction was stirred at room temperature overnight. One milliliter of methanol was added. The reaction was taken to an oil and chromatographed on silica gel by elution with CH$_2$Cl$_2$:EtOAc (9:1 v/v). The desired product was collected as an oil. The oil, 1-(3'-chloro-2'-deoxy-5'-trityl-threo-β-D-ribofuranosyl)-5-trifluoromethyluracil, was deblocked by dissolving in nitromethane (80 mL) and adding zinc bromide (4.45 g) dissolved in nitromethane (80 mL) by the method of V. Kohli, et al. (Tetrahedron Letters, 21, p 2683, 1980). The reaction was stirred at room temperature overnight. More zinc bromide (3.0 g) was added the next day and the reaction was allowed to go overnight. A final addition of zinc bromide (3.7 g) with gentle heating pushed the reaction to a stopping point. The reaction was poured into 1M ammonium acetate. The product was extracted into dichloromethane. The dichloromethane was removed in vacuo and the resulting oil was chromatographed on silica gel by elution with CH$_2$Cl$_2$:MeOH (95:5 v/v). The final product was obtained by treating 1-(3'-chloro-2'-deoxy-β-D-ribofuranosyl)-5-trifluoromethyluracil (0.48 g, 1.53 mMol) with lithium azide (0.19 g, 3.8 mMol) in dimethylacetamide (4.8 mL). The reaction was heated at 90° C. for four hours. The reaction was taken to an oil and chromatographed on silica gel by elution with CHCl$_3$:MeOH (95:5 v/v). Chromatography was required a second time. Elution on silica gel with CH$_2$Cl$_2$:MeOH (97:3 v/v) resulted in a substantially pure product. Crystallization from toluene produced the pure product in 10% yield.

EXAMPLE 35

3'-Azido-2',3'-dideoxycytidine

3'-Azido-2',3'-dideoxycytidine was prepared from 3'-azido-2',3'-dideoxyuridine (2.2 g, 7.9 mMol) as the HCl salt by the procedure of T. A. Krenitsky, et al. (J. Med. Chem., 26, 891, (1983)). The yield was 40%; mp=174.5°-176.5° C.

EXAMPLE 36

3'-Azido-2',3'-dideoxy-5-methylcytidine

3'-Azido-2',3'-dideoxy-5-methylcytidine was prepared from 3'-azido-3'-deoxythymidine (0.8 g, 3.0 mMol) by the procedure of Example 35. The yield was 19%.

EXAMPLE 37

Threo 3'-Azido-2',3'-dideoxycytidine

The synthesis of threo 3'-azido-2',3'-dideoxyctidine was accomplished from 2'-deoxyuridine in four steps.

The 5'-hydroxyl group of 2'-deoxyuridine was tritylated by the method described in Synthetic Procedures in Nucleic Acid Chemistry, 1, 321, (1968).

Threo 3'-Azido-2',3'-dideoxy-5'-trityluridine was prepared by reacting 2'-deoxy-5'-trityluridine (5.0 g, 10.6 mMol) with triphenylphosphine (3.07 g, 11.7 mMoles, 1.1 eq.) and carbon tetrabromide (3.88 g, 11.7 mMol, 1.1 eq.) and lithium azide (5.21 g, 106 mMol, 10 q.) in DMF (80 mL). The carbon tetrabromide was added last. The reaction was allowed to go at room temperature overnight. Methanol (5 mL) was added. The solution was taken to an oil in vacuo and flash chromatographed on silica gel by elution with ethyl acetate. Deblocking the 5'-hydroxyl position was accomplished by heating in 80% acetic acid on a steambath for twenty minutes. Upon cooling, the tritylcarbinol precipitated and was filtered off. The filtrate was taken to dryness and slurried in ethyl ether. The product, threo 3'-azido-2',3'-dideoxyuridine, was carried on without further purification. The final product, threo 3'-azido-2',3'-dideoxycytidine as the HCl salt, was prepared from the uridine analogue by exactly the same procedure as used for the preparation of the erythro isomer (T. A. Krenitsky, et al., J. Med. Chem., 26, 891, (1983)). The yield was 0.021 g, 7%.

EXAMPLE 38

9-(3'-Azido-2',3'-dideoxy-α-D-ribofuranosyl)adenine 9-(3'-Azido-2',3'-dideoxy-α-D-ribofuranosyl)adenine was prepared in two steps from N6-octanoyladenine (2.0 g, 7.7 mMol) and 3'-azido-3'-deoxythymidine (1.13 g, 4.2 mMol) by the procedure described by M. Imazawa and F. Eckstein (J. Org. Chem., 43, 3044 (1978)); mp=120°-122° C.

UV pH 1 λmax 258 nm λmin 230 nm pH 13 λmax 260 nm λmin 229 nm.

CHN for $C_{10}H_{12}N_8O_2$ Calculated: C-43.48; H-4.38; N-40.56. Found: C-43.28; H-4.45; N40-.38.

EXAMPLE 39

9-(3'-Azido-2',3'-dideoxy-β-D-ribofuranosyl)adenine 9-(3'-Azido-2',3'-dideoxy-β-D-ribofuranosyl)adenine was prepared in two steps from N6-octanoyladenine (2.0 g, 7.7 mMol) and 3'-azido-3'-deoxythymidine (1.13 g, 4.2 mMol) by the procedure described by M. Imazawa and F. Eckstein, J. Org. Chem., 43, 3044 (1978).

mp=184°-185° C.

UV pH 1 λmax 257 nm λmin 230 nm pH 13 λmax 260 nm λmin 228 nm.

CHN calculated for $C_{10}H_{12}N_8O_2$ Calculated: C-43.48; H-4.38; N-40.56. Found: C-43.33; H-4.45; N-40.41.

EXAMPLE 40

5'-Acetyl-3'-azido-3-benzoyl-3'-deoxythymidine

5'-Acetyl-3'-azido-3'-deoxythymidine (0.75 g, 2.4 mMol) was dissolved in pyridine (5 mL) and benzoyl chloride (1.4 mL, 12 mMol, 5 eq.) was added at room temperature. The reaction was stirred overnight then poured onto ice water (250 mL). The pH of the aqueous solution was adjusted to 1. The product was extracted with chloroform. The organic phase was washed with water, dried with MgSO4 and filtered. The chloroform was removed and the oily product was flash chromatographed on silica gel eluted with chloroform. The product was collected as an oil.

H¹NMR (DMSO-d6): δ8.04-7.5 (m,6H;3N-benzoyl and 6H), δ6.12 (dd,1H,$J_{1',2a'}$=5.6 Hz, $J_{1',2b'}$=6.7 Hz, 1'H), δ4.55-3.96 (m, 4H; 3'H,4'H,5H'), δ2.62-2.38 (m,2H,2'H), δ2.07 (s,3H,5' acetyl CH3), δ1.90 (d, 3H, $J_{5,6}$=1.0 Hz, 5CH3).

CHN calculated for $C_{19}H_{19}N_5O_6$ Calculated: C-55.20; H-4.63; N-16.94. Found: C-55.29; H-4.64; N-16.93.

EXAMPLE 41

Threo-3'-Azido-5-bromo-2',3'-dideoxyuridine

Threo 3'-Azido-5-bromo-2',3'-dideoxyuridine was prepared from 2'-deoxyuridine by a five step reaction sequence.

Protection of the 5'-hydroxyl group of 2'-deoxyuridine with a triphenylmethyl group was accomplished in the usual manner. The 3'-hydroxyl was mesylated. A 3'-azido group was introduced with the correct stereochemistry by adding 2'-deoxy-3'-mesyl-5'-trityluridine (22 g, 40 mMol) to a solution of sodium azide (7.84 g, 120 mMol, 3 eq.) in dimethylformamide (380 mL) at 80° C. The reaction was continued for 35 hours. The solution was poured onto ice water (2 L) and the precipitate collected by filtration. The product was isolated by chromatography on silica gel eluted with chloroform:methanol (1:1, v/v) in 51% yield. The 5'-hydroxyl position was deblocked with 80% acetic acid on a steambath for 25 minutes. After cooling, the tritylcarbinol was filtered off. The filtrate was reduced to a thick oil in vacuo. The product was isolated by flash chromatography on silica gel eluted with chloroform:methanol (85:15 v/v). The 5 position of threo-3'-azido-2',3'-dideoxyuridine was brominated by exactly the same procedure as outlined for the bromination of erythro-3'-azido-2',3'-dideoxyuridine.

UV pH 1 λmax 280, ε=9400, λmin 244, ε=2600 pH 13 λmax 276 ε=6700, λmin 251 ε=3700.

H¹NMR (DMSO-d6): δ11.86 (s,1H,3-NH), δ8.02 (s,1H,6H), δ5.99 (dd,1H,$J_{1',2a'}$=3.0 Hz; $J_{1',2b'}$=7.5 Hz, 1'H), δ5.1 (t,1H, $J_{5'}CH_2$ 5'OH=5.4 Hz, 5'OH), δ4.49 (m,1H,3'H), δ4.05 (m,1H,4'H), δ3.71 (m,2H,5'H), δ2.72 (m,1H, 2b'), δ2.18 (m,1H,2a').

CHN for $C_9H_{10}BrN_5O_4$-0.25 $H_2O$-0.1 $C_2H_4O_2$ Calculated: C-32.25; H-3.21; N-20.44; Br-23.32. Found: C-32.17; H-3.21; N-20.33; Br-23.19.

EXAMPLE 42

1-(3'-Azido-2',3'-dideoxy-β-D-erythro-pentofuranosyl)-2-(benzyloxo)-5-methyl-4-(1H)-pyrimidinone Sodium (0.4 g, 17.4 mMol, 2.6 eq.) was allowed to react with dry benzyl alcohol (10 mL) for one hour at room temperature. 2,5'-O-Anhydro-3'-azido-3'-deoxythymidine (1.65 g, 6.6 mMol) was added. The reaction was allowed to continue for one hour. After pouring onto ice water (250 mL), the pH was adjusted to 7 and the aqueous phase was extracted with ethyl acetate. The organic phase was extracted with water (4 times). After drying with MgSO4 the ethyl acetate was removed in vacuo. The resultant oil was chromatographed on silica gel, eluted first with ethyl acetate then with ethyl acetate:methanol (9:1 v/v). The product-containing fractions was collected and the solvents removed in vacuo, yielding an oil. The oil crystallized after covering with ethyl ether; m.p.=125°-126.5° C.

UV pH 1 unstable pH 13 λmax 256, ε=10700, λmin 240, ε=8900.

H¹NMR (DMSO-d6): δ7.8 (d,1H,$J_{65}$=1.2 Hz, 6H), δ7.49-7.38 (m,5H,2-phenyl), δ6.08 (dd,1H,$J_{1',2a'}$=5.0 Hz; $J_{1',2b'}$=7.0 Hz, 1'H), δ5.37 (s,2H,2CH2), δ5.25 (t,1H,$J_{5'}CH_25'OH$=5.4 Hz, 5'OH) δ4.36-4.32 (m,1H,3'H), δ3.85-3.81 (m,1H,4'H), δ3.7-3.58 (m,2H,5'H), δ2.53-2.34 (m,2H,2'H), δ1.82 (d,3H,$J_{5,6}$=1.0 Hz, 5CH3).

CHN for $C_{17}H_{19}N_5O_4$ Calculated: C-57.14; H-5.36; N-19.60. Found: C-57.02; H-5.43; N-19.53.

EXAMPLE 43

1-(3'-Azido-2',3'-dideoxy-β-D-threo-pentofuranosyl)-2-ethoxy-5-methyl-4-(1H)-pyrimidinone Threo 3'-Azido-5'-O-mesylthymidine (1.08 g, 3.13 mMol) [prepared from threo-3'-azidothymidine] was dissolved in 100 mL EtOH and treated with NaHCO3 (0.26 g, 3.13 mMol) at reflux for 18 hours. The reaction was cooled and filtered. The solvents were removed in vacuo and the residue placed on a silica gel column followed by elution with 9:1 (v/v) CHCl3/MeOH. Combination of appropriate fractions and removal of solvents in vacuo yielded 0.7 g (2.4 mMol, 75.7%); mp=120°-122° C.

UV (nm): at pH 1 λmax=260 (ε=9300), λmin=237 (ε=5500), λshoulder=221 (ε=7500); at pH 13 λmax=256 (ε=10000), λmin=240 (ε=7700).

H$^1$NMR (DMSO-d$_6$) δ7.58 (s,1H,H6), δ6.0 (dd,1H,H1', J=2.9, 4.56 Hz), δ5.06 (t,1H,5'OH, J=4.91 Hz), δ4.51–4.47 (m,1H,H3'), δ4.34 (q,2H,—OCH$_2$—, J=7.14 Hz), δ4.10–4.05 (m,1H,H4'), δ3.73 (t,2H,H5', J=5.62 Hz), δ2.82–2.73 (m,1H,H2'b), δ2.21–2.14 (m,1H,H2'a), δ1.82 (s,3H,5CH$_3$), δ1.31 (t,3H,—CH$_2$—CH$_3$, J=6.65 Hz).

Analysis for C$_{12}$H$_{17}$N$_5$O$_4$ Calculated: C 48.81, H 5.80, N 23.72. Found: C 48.59, H 5.86, N 23.64.

EXAMPLE 44

Threo 3'-Azido-2',3'-dideoxy-4-thiothymidine

Threo 3'-Azido-5'-O-trityl-3'-deoxy-4-(1,2,4-triazole)thymidine (1.25 g, 2.2 mMol) (prepared according to the method of W. Sung, Nucleic Acids Research (1981), 9, 6139) was dissolved in 100 mL acetone and 30 mL H$_2$O then treated with 0.22 g NaSH.xH$_2$O. The mixture was stirred for 3 hours. The volume was reduced by half and extracted with 300 mL CHCl$_3$. The CHCl$_3$ was washed with 50 mL H$_2$O, dried over Na$_2$SO$_4$, then removed in vacuo to yield an oil. The 5'-O-trityl group was removed by dissolving this oil in 100 mL 80% HOAc. The solution was heated on a steam bath for 2 hours then cooled, diluted with 100 mL H$_2$O and filtered. The solvents were removed in vacuo and the oil placed on a silica gel column. Elution with 20:1 (v/v) CHCl$_3$/MeOH, collection of appropriate fractions followed by removal of solvents in vacuo yielded 0.18 g (0.62 mMol; 28%); mp=65°–67° C.

UV (nm): at pH 1 λmax=337 (ε=20700), λmin=280 (ε=1200), λshoulder=238 (ε=3400);

at pH 13 λmax=320 (ε=18400), λmin=257 (ε=1700);

H$^1$NMR (DMSO-d$_6$) δ7.63 (s,1H,H1', J=2.93, 4.89 Hz), δ5.06 (s,1H,5'OH), δ4.50–4.46 (m,1H,H3'), δ4.10–4.04 (m,1H,H4'), δ3.73 (d,2H,H5', J=5.61 Hz), δ2.78–2.68 (m,1H,H2'b), δ2.20–2.14 (m,1H,H2'a), δ2.00 (s,3H,5CH$_3$).

Analysis for C$_{10}$H$_{13}$N$_5$O$_3$S 0.1 C$_2$H$_6$O-0.25 H$_2$O Calculated: C 41.90, H 4.86, N 23.95, S 10.97. Found: C 41.99, H 4.73, N 23.88, S 10.91.

EXAMPLE 45

4-Amino-3'-azido-5-bromo-2',3'-dideoxyuridine

3'-Azido-2',3'-dideoxyuridine was acetylated and brominated according to the method of Visser (Synthetic Procedures in Nucleic Acid Chemistry Vol. 1 p. 410) to give 5'-acetyl-3'-azido-5-bromo-2',3'-dideoxyuridine. This material was reacted with 5 equivalents of 1,2,4-triazole and two equivalents of 4-chlorophenyl dichlorophosphate in dry pyridine at ambient temperature for 7 days to give 5'-acetyl-3'-azido-5-bromo-4-(1,2,4-triazolyl)-2',3'-dideoxyuridine as a yellow oil, in moderate yield. Treatment at ambient temperature with ammonia saturated methanol at 0° C. for 18 hours gave, after ethyl acetate recrystallization and filtration of the resultant crystals, 4-amino-3'-azido-5-bromo-2',3'-dideoxyuridine 173 mg (0.5 mMol, 6.3%); mp=162°–165° C. (dec).

UV (nm): at pH 1 λmax=300,215 (ε=10700, 12100), λmin=253 (ε=1500); at pH 13 λmax=288 (ε=7300) λmin=260 (ε=3900)

H$^1$NMR (DMSO-d$_6$) δ8.3 (s, 1H, H6), δ7.85 (broad s, 1H, 4-NH$_2$), δ7.05 (broad s, 1H, 4-NH$_2$), δ6.0 (t, 1H, H1', J=5.94 Hz), δ5.33 (t, 1H, 5'-OH, J=5.01 Hz), δ4.4–4.3 (m, 1H, H3'), δ3.9–3.5 (m, 3H, H4', H5'), δ2.31 (t, 2H,H2', J=6.27 Hz).

Analysis for C$_9$H$_{11}$N$_6$O$_3$Br Calculated: C 32.64, H 3.35, N 25.38, Br 24.13. Found: C 32.52, H 3.41, N 25.32, Br 24.04.

EXAMPLE 46

3'-Azido-5-bromovinyl-2',3'-dideoxyuridine

5-Bromovinyl-2'-deoxyuridine (BVDU) was synthesized using the method of Jones, et al. (Tetrahedron Letters 45, 4415 (1979)) with similar yields. BVDU was tritylated and mesylated by the method of Horwitz et al., J. Org. Chem, 31, 205 (1966). This product was treated with an equimolar amount of sodium bicarbonate in refluxing methanol to yield the 3',2-O-anhydro-5-bromovinyl-2'-deoxyuridine. This product was treated with 3 equivalents of lithium azide in 1% water/dimethyl formamide at 130° C. Silica gel chromatography of the crude material followed by combination and evaporation of appropriate fractions afforded 3'-azido-5-bromovinyl-2',3'-dideoxyuridine as a golden oil;

UV (nm); at pH 1 λmax=292,247 λmin=270,238; at pH 13 λmax=253, λmin=238, λsh=284;

H$^1$NMR (DMSO-d$_6$) δ8.06 (s, 1H, H$_6$), δ7.25 (d, 1H, —CH=CHBr, J=13.4 Hz) δ6.85 (d, 1H, =CHBr, J=13, 7 Hz) δ6.07 (t, 1H, H$_{1'}$, J=6.3 Hz), δ5.30 (broad s, 1H, 5'-OH), δ4.42 (q, 1H, H$_{3'}$, J=6.3, 6.1 Hz), δ3.86–3.82 (m, 1H, H$_{4'}$), δ3.68–3.59 (m, 2H, H$_{5'}$), δ2.47–2.32 (m, 2H,H$_{2'}$).

Analysis for C$_{11}$H$_{12}$N$_5$O$_4$Br Calculated: C, 36.89; H, 3.38; N, 19.55. Found: C. 36.86; H, 3.41; N, 19.51.

EXAMPLE 47

Threo 3'-Azido-5-chloro-2',3'-dideoxyuridine

The title compound was prepared in an analogous manner to 3'-azido-5-chloro-2',3'-dideoxyuridine (Example 31) to yield 0.15 g (0.5 mMol, 25%); m.p.=65° C.

UV (nm); at pH 1 λmax=278, 212 (ε=8900), λmin=240 (ε=1600); at pH 13 λmax=275 (ε=6600), λmin=248 (ε=3300);

H$^1$NMR (DMSO-d$_6$) δ11.89 (s, 1H, NH), δ7.94 (s, 1H, H$_6$), δ6.00 (dd, 1H, H$_{1'}$, J=2.93, 4.64 Hz), δ5.1 (t, 1H, 5'OH,J=5.1 Hz), δ4.50–4.46 (m, 1H, H$_{3'}$), δ4.08–4.03 (m, 1H, H$_{4'}$), δ3.71 (t, 2H, H$_{5'}$, J=5.32 Hz), δ2.77–2.67 (m, 1H, H$_{2'}$b), δ2.23–2.16 (m, 1H, H$_{2'}$a).

Analysis for C$_9$H$_{10}$N$_5$O$_4$Cl 0.1 H$_2$O-0.1 C$_4$H$_8$O$_2$ Calculated: C, 37.85; H, 3.72; N, 23.48; Cl, 11.89. Found: C, 37.94; H, 3.91; N, 23.23.; Cl, 11.86.

EXAMPLE 48

1-(3'-Azido-2',3'-dideoxy-β-D-erythro-pentofuranosyl)-5-methyl-2-(pentyloxo)-4-(1H)-pyrimidinone 1-(3'-Azido-2',3'-dideoxy-β-D-erythro-pentofuranosyl)-5-methyl-2-(pentyloxo)-4-(1H)-pyrimidinone was prepared by the method used to prepare 1-(3'-azido-2',3'-dideoxy-β-D-erythro-pentofuranosyl)-2-(benzyloxo)-5-methyl-4-(1H)-pyrimidinone (Example 42). Final purification was by HPLC on C18 eluted with water:methanol (3:7). The solvents were evaporated to collect the product as an oil.

UV pH 1 λ$_{max}$ 258 nm ε=9400, λ$_{min}$ 232 nm ε=5900 pH 13 λ$_{max}$ 256 nm ε=10600, λ$_{min}$ 239 nm ε=8200.

NMR taken in DMSO-d6.

NMR: δ7.81 (s,1H,6H), δ6.04 (t,1H,J$_{1',2'}$=6.7 Hz, 1'H) δ5.28 (t,1H,J$_{5'CH_2,5'OH}$=5.1 Hz,5'OH) δ4.43–4.37 (m,1H,3'H), δ4.27 (t,2H,J$_{2-O(1CH_2,2CH_2)}$=6.6 Hz 2-

O(CH$_2$)$_1$) δ3.88–3.84 (m,1H,4'H), δ3.70–3.50 (m,2H,5'CH$_2$) δ2.50–2.34 (m,2H,2'H), δ1.80 (s,3H,5CH$_3$), δ1.72–1.68 (m,2H,2-O(CH$_2$)$_2$), δ1.38–1.30 (m,4H,2-O(CH$_2$)$_3$ and $_4$) δ0.92–0.87 (m,3H,2-O(CH$_3$)$_5$).

CHN for C$_{15}$H$_{23}$N$_5$O$_4$ ¼ H$_2$O Calculated: C-52.70; H-6.93; N-20.48. Found: C-52.63; H-6.92; N-20.48.

EXAMPLE 49

3'-Azido-3-benzoyl-3'-deoxy-5'-mesylthymidine

3'-Azido-3-benzoyl-3'-deoxy-5'-mesylthymidine was prepared from 3'-azido-3'-deoxy-5'-mesylthymidine by an analogous method to that used in Example 40 to prepare 5'-acetyl-3'-azido-3-benzoyl-3'-deoxythymidine from 5'-acetyl-3'-azido-3'-deoxythymidine; m.p.=86°–88° C.

UV pH 1 $\lambda_{max}$ 259 nm $\epsilon$=21200, $\lambda_{min}$ 230 nm $\epsilon$=6400 pH 13 $\lambda_{max}$ 265 nm $\epsilon$=9600, $\lambda_{min}$ 248 nm $\epsilon$=8000.

H$^1$NMR (DMSO-d$_6$) δ8.00–7.58 (m,6H,6H and phenyl), δ6.15 (t,1H,J$_{1',2'}$=6.1 Hz,1'H) δ4.55–4.47 (m,3H; 3'H and 5'CH$_2$), δ4.12–4.10 (m,1H,4'H) δ3.28 (s,3H,5'-SO$_2$CH$_3$), δ2.65–2.4 (m,2H,2'H), δ1.89 (d,3H,J$_{5,6}$=1.3 Hz, 5CH$_3$).

CHN for C$_{18}$H$_{19}$N$_5$O$_7$S Calculated: C-48.10; H-4.26; N-15.58: S-7.13. Found: C-48.00; H-4.23; N-15,39; S-7.10.

EXAMPLE 50

Threo 3'-Azido-2',3'-dideoxy-5-iodouridine

5-Iodo-2'-deoxyuridine was tritylated and mesylated according to Horwitz et al. (J. Org. Chem, 31, (1966), 205). This product was heated with 3 equivalents of lithium azide in anhydrous dimethyl formamide at 74° C. for 48 hours. Silica gel chromatography of the reaction mixture with 20:1 CHCl$_3$/MeOH (v/v) followed by combination and evaporation of appropriate fractions gave threo 3'-azido-2',3'-dideoxy-5-iodo-5'-trityluridine. The 5'-hydroxyl was deblocked with a saturated zinc bromide/nitromethane solution at 0° C. Silica gel chromatography of the crude product using 9:1 CHCl$_3$/MeOH (v/v) followed by combination and evaporation of the appropriate fractions afforded threo3'-azido-2',3'-dideoxy-5-iodouridine as a solid; m.p.=80° C.

UV (nm); at pH 1 $\lambda_{min}$=247; at pH 13 $\lambda_{max}$=277, $\lambda_{min}$=252;

H$^1$NMR (DMSO-d$_6$) δ8.37 (s, 1H, H6), δ6.00 (t, 1H, H1', J=6.17 Hz), δ5.4–5.3 (m, 1H, 5' OH), δ4.4–4.3 (m, 1H, H3'), δ3.9–3.8 (m, 1H, H4'), δ3.7–3.6 (m, 2H, H5').

Analysis for C$_9$H$_{10}$N$_5$O$_4$I 0.4 C$_4$H$_8$O$_2$ Calculated: C 30.73, H 3.21, N 16.90, I 30.63. Found: C 30.93, H 3.09, N 16.61, I 30.94.

EXAMPLE 51

1-(5'-O-Acetyl-3'-azido-2',3'-dideoxy-β-D-erythro-pentofuranosyl)-5-methyl-4-(1,2,4-triazol-1-yl)-2(1H)-pyrimidinone 5'-Acetyl-3'-azido-3'-deoxythymidine was reacted with 5 equivalents of 1,2,4-triazole and two equivalents of 4-chlorophenyl dichlorophosphate in dry pyridine at ambient temperature for 10 days. Silica gel chromatography of the crude product using 1:1 EtOAc/hexane (v/v) followed by combination and evaporation of the appropriate fractions yielded an oil. Crystallization from EtOAc afforded the title compound as a solid 2.7 g (7.5 mMol; 60%); m.p.=143°–145° C.

UV (nm): at pH 1 $\lambda_{max}$=324,245,215 ($\epsilon$=9300, 10000, 20500), $\lambda_{min}$=282,233 ($\epsilon$=2100,8200);

at pH 13 $\lambda_{max}$=276 ($\epsilon$=6000), $\lambda_{min}$=242 ($\epsilon$=2000).

H$^1$NMR (DMSO-d$_6$) δ9.34, 8.40 (2s, 2H, triazolyl), δ8.23 (s, 1H, H6), δ6.12 (t, 1H, H1', J=6.16 Hz), δ4.48–4.17 (m, 4H, H3', H4',H5'), δ2.35 (s, 3H, 5'-acetyl), δ2.07 (s, 3H, 5CH$_3$).

Analysis for C$_{14}$H$_{16}$N$_8$O$_4$ Calculated: C, 46.67; H, 4.48; N, 31.1. Found: C, 46.58; H, 4.51; N, 31.02.

EXAMPLE 52

1-(3'-Azido-2',3'-dideoxy-β-D-erythro-pentofuranosyl)-4-dimethylamino-5-methyl-2-(1H)-pyrimidine 5'-Acetyl-3'-azido-3'-deoxy-4-(1,2,4-triazolyl)thymidine was dissolved in dry acetonitrile at ambient temperature under a nitrogen atmosphere. Dimethylamine, 20 equivalents, was added all at once and the reaction stirred for 30 minutes. The solvents were removed, the residue dissolved in ammonia-saturated methanol and the solution stirred for 30 minutes. The solvents were removed and the residue dissolved in EtOAc. The title compound slowly precipitated from solution and was filtered off to give a white solid; mp=157°–159° C.

UV (nm): at pH 1 $\lambda$max=299,224 ($\epsilon$=14900,7900) $\lambda$min=254 ($\epsilon$=2500); at pH 13 $\lambda$max=287 ($\epsilon$=14000), $\lambda$min=243 ($\epsilon$=6800).

H$^1$NMR (DMSO-d$_6$) δ7.63 (s,1H,H6), δ6.06 (t,1H,H1',J=6.53 Hz), δ5.22 (t,1H,5'OH,J=5.2 Hz), δ4.37–4.34 (m,1H,H3'), δ3.83–3.8 (m,1H,H4'), δ3.65–3.6 (m,2H,H5'), δ3.06 (s,6H,N(CH3)2), δ3.29–2.23 (m,2H,H2'), δ2.11 (s,3H,5-CH$_3$).

Analysis for C$_{12}$H$_{18}$N$_6$O$_3$ Calculated: C 48.97, H 6.16, N 28.56. Found: C 49.06, H 6.2, N 28.5.

EXAMPLE 53

1-(3'-Azido-2',3'-dideoxy-β-D-erythro-pentofuranosyl)-5-methyl-2-(isopentyloxo)-4-(1H)-pyrimidinone The title compound was prepared by an analogous method to that used to prepare 1-(3'-azido-2',3'-dideoxy-β-D-erythro-pentofuranosyl)-2-(benzyloxo)-5-methyl-4-(1H)-pyrimidinone (Example 42).

UV pH 1(nm) $\lambda$max 258 $\epsilon$=9000, $\lambda$min 237 $\epsilon$=6000 pH 13 (nm) $\lambda$max 255 $\epsilon$=11000, $\lambda$min 239 $\epsilon$=8000.

H$^1$NMR (DMSO-d$_6$): δ7.79 (s,1H,6H), δ6.02 (t,1H,J$_{1',2'}$=6.3 Hz, 1'H), δ5.23 (t,1H,J$_{5'OH,5'H}$=5.2 Hz, 5'OH), δ4.4–4.3 (m,3'H and 2-O—CH$_2$—CH$_2$CH(CH$_3$)$_2$), δ3.9–3.8 (m,1H,4'H), δ3.7–3.5 (m,2H,5'H), δ2.5–2.3 (m,2'H) δ1.78 (s,3H,5CH$_3$), δ1.7–1.5 (m,3H,2-OCH$_2$—CH$_2$—CH(CH$_3$)$_2$) δ0.92 and 0.89 (d,6H,J=6.3 Hz,2-O(CH$_2$)$_2$CH(CH$_3$)$_2$).

CHN for C$_{15}$H$_{23}$N$_5$O$_4$ Calculated: C-53.40, H-6.87, N-20.76. Found: C-53.14, H-6.92, N-20.62.

EXAMPLE 54

3-Acetyl-3'-azido-5'-O-(3-chlorobenzoyl)-3'-deoxythymidine

To a mixture of 3'-azido-5'-O-(4-chlorobenzoyl)-3'-deoxythymidine (0.3 g, 0.74 mMol) and silver cyanide (0.4 g, 3.0 mMol) in 20 mL of benzene, excess acetyl chloride (2.6 g, 33 mMol) was added in several portions. The mixture was stirred at room temperature until the starting material disappeared (4 hours) as established by TLC CHCl$_3$/MeOH 20:1 (v/v). The reaction was filtered and the filtrate evaporated under reduced pressure to dryness. The resulting oily residue was chromatographed on silica gel eluted with chloroform/hexane 1:1 (v/v) followed by chloroform to give 0.21 g (64%) of the desired product as an oil.

UV (nm): at pH 1 λmax 273 (ε=9000), λmin 251 (ε=6200); pH 13 λmax 266 (ε=8800), λmin 247 (ε=7000).

H$^1$NMR (DMSO-d$_6$) δ1.68 (s, 3H, 5-CH$_3$), δ2.47 (s, 3-COCH$_3$), δ2.3–2.5 (m, 2'H), δ4.1–4.2 and 4.4–4.7 (m, 4H,3'H, 4'H and 5'H), δ6.1 (t, 1H, J$_{1',2'}$=6.3 Hz, 1'H), δ7.5–8.0 (m, 5H, 6H and phenyl).

Analysis for C$_{19}$H$_{18}$N$_5$O$_6$Cl·0.2 CHCl$_3$ Calculated: C, 48.89; H, 3.89; N, 14.85; Cl, 12.03. Found: C, 49.05; H, 3.94; N, 14.79; Cl, 12.56.

EXAMPLE 55

3'-Azido-5-cyano-2',3'-dideoxyuridine

5-Iodo-2',3'-dideoxyuridine was reacted with acetic anhydride (2.1 equivalents) in pyridine with exclusion of moisture at ambient temperature for 2 hours to give 2',3'-dideoxy-3',5'-diacetyl-5-iodouridine. The nucleoside (1 equivalent), potassium cyanide (1.3 equivalents), and potassium acetate (1.3 equivalents) were combined in dry DMSO and heated at 97° C. under nitrogen for 2 hours. The solvents were removed in vacuo and the residual oil applied to a silica gel column followed by elution with 1:1 CHCl$_3$/EtOAc (v/v). The appropriate fractions were collected, combined and evaporated to give 5-cyano-2',3'-dideoxy-3',5'-diacetyluridine. The compound was dissolved in ammonia-saturated methanol and stirred at 0° C. for 18 hours. The solvents were removed in vacuo at ambient temperature to give crystals of the title compound; mp=160°–162° C.

UV (nm): at pH 1 λmax=276,215 (ε=13500,11200), λmin=238 (ε=1700); at pH 13 λmax=276 (ε=10100), λmin=240 (ε=3400)

H$^1$NMR (DMSO-d$_6$) δ8.81 (s,1H,H6), δ6.00 (t,1H,H1', J=5.94 Hz), δ5.3–5.21 (m,2H,5'OH,3'OH), δ4.28–4.15 (m,1H,H3'), δ3.82–3.77 (m,1H,H4'), δ3.7–3.5 (m,2H,H5'), δ2.18 (t,2H,H2', J=5.75 Hz).

Analysis for C$_{10}$H$_{11}$N$_3$O$_5$ 0.25H20 Calculated: C 46.61, H 4.50, N 16.31. Found: C 46.67, H 4.71, N 16.54.

EXAMPLE 56

1-(3'-Azido-2',3'-dideoxy-β-D-threo-pentofuranosyl)-5-methyl-2-pentyloxy-4-(1H)-pyrimidinone 2,5'-O-Anhydro-1-(3'-azido-2',3'-dideoxy-β-D-threo-pentofuranosyl)thymine was added to a solution of potassium t-butoxide (0.5 equivalents) in pentan-1-ol. The reaction was stirred for 2 hours at ambient temperature under nitrogen. The solvents were removed in vacuo and the residue applied to a silica gel column. Elution with 20:1 CHCl$_3$/MeOH (v/v) followed by combination and evaporation of the appropriate fractions yielded a clear oil which slowly formed crystals of the title compound upon standing; mp=110°–111° C.

UV (nm): at pH 1 λmax=255 (ε=10200), λmin=237 (ε=6200), λsh=222 (ε=9000); at pH 13 λmax=251,226 (ε=11600,9600), λmin=238 (ε=8600)

H$^1$NMR (DMSO-d$_6$) δ7.58 (s,1H,H6), δ5.98 (dd,1H,H1',J=2.98, 4.88 Hz), δ5.07 (t,1H,5'OH,J=5.42 Hz), δ4.5–4.47 (m,1H,H3'), δ4.31–4.25 (m,2H,-OCH$_2$—), δ4.1–4.06 (m,1H,H4'), δ3.73 (t,2H,H5',J=5.62 Hz), δ2.82–2.72 (m,1H,H2'), δ2.2–2.14 (m,1H,H2'), δ1.82 (s,3H,5-CH$_3$), δ1.75–1.65 (m,2H,pentyl), δ1.4–1.3 (m,4H,pentyl), δ0.92–0.87 (m,3H,pentyl).

Analysis for C$_{15}$H$_{23}$N$_4$O$_4$ Calculated: C 53.40, H 6.87, N 20.76. Found: C 53.31, H 6.90, N 20.74.

EXAMPLE 57

1-(3'-Azido-2',3'-dideoxy-β-D-threo-pentofuranosyl)-2-benzyloxy-5-methyl-4(1H)-pyrimidinone The title compound was prepared in a manner analogous to that described for 1-(3'-azido-2',3'-dideoxy-β-D-threo-pentofuranosyl)-5-methyl-2-pentyloxy-4-(1H)-pyrimidinone (Example 56) using benzyl alcohol in place of pentan-1-ol; mp=137°–139° C.

UV (nm): at pH 1 λmax=266 (ε=9100), λmin=235 (ε=3000); at pH 13 λmax=256 (ε=11500), λmin=240 (ε=9600).

H$^1$NMR (DMSO-d6) δ7.6 (s,1H,H6), δ7.49–7.37 (m,5H,phenyl), δ6.01 (dd,1H,H1', J=2.5,2.5,5.0 Hz), δ5.35 (s,2H,benzyl), δ5.1–5.0 (m,1H,5'OH), δ4.5–4.4 (m,1H,H3'), δ4.1–4.0 (m,1H,H4'), δ3.77–3.67 (m,2H,H5'), δ2.85–2.70 (m,1H,H2'), δ2.25–2.15 (m,1H,H2') δ1.83 (s,3H,5-CH$_3$).

Analysis for C$_{17}$H$_{19}$N$_5$O$_4$ 0.25H$_2$O. Calculated: C 56.43, H 5.43, N 19.35. Found: C 56.51, H 5.37, N 19.36.

EXAMPLE 58

1-(3'-Azido-2',3'-dideoxy-β-D-erythro-pentofuranosyl)-4-methoxy-5-methyl-2(1H)-pyrimidinone 5'-Acetyl-3'-azido-3'-deoxy-4-(1,2,4-triazolyl)thymidine was treated at ambient temperature with 0.5N sodium methoxide in methanol for 24 hours. The solution was neutralized to pH 7 with a sulphonic acid resin (DOW 50 W, H+), the resin filtered off and the filtrate evaporated to a solid in vacuo. This solid was dissolved in a small amount of CHCl$_3$, applied to a silica gel column and eluted with 2% MeOH in CHCl$_3$. The appropriate fractions were collected, combined and evaporated to dryness to yield a white solid; mp=119°–123° C.

UV (nm): at pH 1 λmax=279 (ε=7500), λmin=239 (ε=1700); at pH 13 λmax=279 (ε=6400), λmin=243 (ε=1300).

H$^1$NMR (DMSO-d$_6$) δ8.02 (s,1H,H6), δ6.08 (t,1H,H1', J=5.86 Hz), δ5.29 (t,1H,5'OH,J=5.48 Hz), δ4.41–4.33 (m,1H,H3'), δ3.9–3.86 (m,1H,H4'), δ3.86 (s,3H,4-OCH$_3$), δ3.75–3.58 (m,2H,H5'), δ2.4–2.3 (m,2H,H2'), δ1.89 (s,3H,5-CH$_3$).

Analysis for C$_{11}$H$_{15}$N$_5$O$_4$ Calculated: C 46.97, H 5.38, N 24.9. Found: C 47.06, H 5.40, N 24.86.

EXAMPLE 59

1-(3'-Azido-2',3'-dideoxy-β-D-erythro-pentofuranosyl)-5-methyl-4-(1-pyrrolidinyl)-2-(1H)-pyrimidinone 5'-Acetyl-3'-azido-3'-deoxy-4-(1,2,4-triazolyl)thymidine was dissolved in dry acetonitrile at ambient temperature under a nitrogen atmosphere. Pyrrolidine, 5 equivalents, was added dropwise over 5 minutes and the reaction stirred for 2 hours. The solvents were removed in vacuo to yield an oil. This oil was dissolved in ammonia-saturated methanol at ambient temperature and stirred for 4 hours. The solvents were removed in vacuo and the residue applied to a silica gel column. Elution with 20:1 CHCl$_3$/MeOH (v/v) followed by combination and evaporation of the appropriate fractions gave the title compound as a white solid; mp=168°–171° C.

UV (nm): at pH 1 λmax=295,233 (ε=15700, 9500), λmin=253 (ε=2600); at pH 13 λmax=285 (ε=15300), λmin=241 (ε=7900).

H$^1$NMR (DMSO-d$_6$) δ7.57 (s,1H,H6), δ6.02 (t,1H,H1', J=6.5 Hz), δ5.22 (t,1H,5'OH,J=5.15 Hz),

δ4.4–4.3 (m,1H,H3'), δ3.84–3.77 (m,1H,H4'), δ3.67–3.51 (m,6H,H5',4 pyrrolidine H's), δ2.24 (t,2H,H2',J=6.08 Hz) δ2.14 (s,3H,5-CH₃), δ1.87–1.78 (m,4H,pyrrolidine).

Analysis for C₁₄H₂₀N₆O₃ Calculated: C 52.49, H 6.29, N 26.23. Found: C 52.37, H 6.33, N 26.17.

EXAMPLE 60

1-(3'-Azido-2',3'-dideoxy-β-D-erythro-pentofuranosyl)-4-benzyloxy-5-methyl-2-(1H)-Pyrimidinone 5'-Acetyl-3'-azido-3'-deoxy-4-(1,2,4-triazolyl)thymidine, dissolved in dry acetonitrile, was added dropwise at ambient temperature under nitrogen over 5 minutes to a suspension of benzyl alcohol (5 equivalents) and potassium t-butoxide (2 equivalents) in dry acetonitrile. The reaction was stirred for one hour and the solvents were removed in vacuo. The residue was put on a silica gel column and eluted with 3:1 CHCl₃/EtOAc (v/v). The appropriate fractions were collected, combined and evaporated to give a solid. The solid was recrystallized from 1:1 CHCl₃/EtOAc (v/v) and the resultant crystals filtered off to yield the title compound; mp=133°–134° C.

UV (nm): at pH 1 λmax=276 (ε=8000), λmin=237 (ε=2000); at pH 13 λmax=281 (ε=8100), λmin=237 (ε=1600).

H¹NMR (DMSO-d₆) δ8.05 (s,1H,H6), δ7.45–7.35 (m,5H,phenyl), δ6.07 (t,1H,H1', J=5.94 Hz), δ5.35 (s,2H,benzyl), δ5.27 (t,1H,5'OH,J=5.20 Hz), δ4.41–4.31 (m,1H,H3') δ3.91–3.83 (m,1H,H4'), δ3.7–3.6 (m,2H,H5'), δ2.4–2.3 (m,2H,H2'), δ1.9 (s,3H,5-CH₃).

Analysis for C₁₉H₂₁N₅O₅ Calculated: C 57.14, H 5.36, N 19.60. Found: C 57.06, H 5.37, N 1958.

EXAMPLE 61

5'-Acetyl-3'-azido-5-bromo-2',3'-dideoxyuridine

3'-Azido-2',3'-dideoxyuridine was acetylated and brominated according to the method of Visser (Synthetic Procedures in Nucleic Acid Chemistry, 1, 410) to give the title compound; mp=112°–114° C.

UV (nm): at pH 1 λmax=279,210 (ε.9500,10600), λmin=243 (ε=2000); at pH 13 λmax=276 (ε=700), λmin=250 (ε=4000).

H¹NMR (DMSO-d₆) δ11.88 (s,1H,NH), δ8.02 (s,1H,H6), δ6.08–6.01 (m,1H,H1'), δ4.47–4.4 (m,1H,H3'), δ4.27–4.24 (m,2H,H5'), δ4.03–4.0 (m,1H,H4'), δ2.41–2.34 (m,2H,H2'), δ2.09 (s,3H,acetyl).

Analysis for C₁₁H₁₂N₅O₅Br Calculated: C 35.31, H 3.23, N 18.72, Br 21.36. Found: C 35.29, H 3.25, N 18.66, Br 21.45

EXAMPLE 62

1-(3'-Azido-2'3'-dideoxy-β-D-threo-pentofuranosyl-5-(trifluoromethyl)uracil

The 5'-hydroxyl group of 5-trifluoromethyl-2'-deoxyuridine was protected with a triphenylmethyl group and the 3'-hydroxyl group mesylated. The product (3.0 g, 4.9 mMol) was reacted at 70° C. with 0.7 g LiN₃ in 50 mL DMF for about 26 hours. The cooled reaction was poured onto ice with stirring. The solid was isolated, washed with H₂O and purified by flash chromatography using hexane/ethyl acetate (2:1 v/v). Combination of the appropriate fractions and removal of the solvent gave 0.83 g of tritylated product. This was dissolved in a saturated solution of zinc bromide in acetonitrile and stirred at 0° C. overnight. After 100 mL ammonium acetate (1M) was added, the organic layer was separated and taken to dryness in vacuo. The residue was purified by flash chromatography using CHCl₃/CH₃OH (20:1 v/v). Fractions were combined and taken to dryness in vacuo. Yield of the title compound was 0.25 g, 0.8 mMol, 5.3%; mp 118°–120° C.

Analysis for C₁₀H₁₀F₃N₅O₄ Calculated: C 37.39, H 3.14, N 21.80, F 17.74. Found: C 37.31, H 3.23, N 21.75, F 17.60.

EXAMPLE 63

1-(3'-Azido-2',3'-dideoxy-β-D-threo-pentofuranosyl)uracil

The 5'-hydroxy group of 2'-deoxyuridine was protected and the 3'-hydroxyl group was mesylated. The 3'-mesyl group was displaced with inversion of configuration by heating in dimethylformamide at 80° C. with lithium azide (3 eq.) for 24 hours. The reaction was poured into ice water and the product precipitated. After filtration the damp product was deblocked. Final purification was by chromatography on silica gel eluted with chloroform/methanol (95:5). The appropriate fractions were combined and the solvents removed to yield the title compound as a solid; mp=142°–145° C.

EXAMPLE 64

1-(3'-Azido-2',3'-dideoxy-β-D-erthyro-pentofuranosyl)uracil

The 5'-hydroxyl group of 2'-deoxyuridine (30 g, 0.13 moles) was tritylated by the method of Horwitz et al. (J. Org. Chem., 31, 205, (1966). The 3'-hydroxyl group (12.6 g, 0.027 moles) was chlorinated by the method of example 62. The dimethylacetamide was removed in vacuo and the thick oil was poured into water (500 ml). The product was extracted with ether (3×). The solvent was removed and the resultant oil chromatographed on silica gel, eluted first with dichloromethane than with 1% methanol in dichloromethane. The product fractions were combined and the solvents removed in vacuo. The 5'-hydroxyl group was deblocked, without further purification, by heating in 80% acetic acid on a steambath for 20 minutes. Upon cooling, tritylcarbinol precipitated and was filtered off. The filtrate was concentrated in vacuo and chromatographed on silica gel eluted with ethyl acetate. The 3'-chloro was displaced by heating in HMPA with lithium azide (3 eq.) at 90° C. overnight. The reaction was poured into water and extracted with chloroform. The chloroform contained the product and was dried with MgSO₄. Removal of the chloroform yielded a solid which was recrystallized first from ethyl acetate/methanol, then water. The recrystallized solids were dissolved in water and applied to a column of XAO. After washing with water the title compound was eluted with ethanol. The ethanol was removed in vacuo to yield a solid; mp=166.5°–168.5° C.

EXAMPLE 65

1-(3'-Azido-2',3'-dideoxy-erythro-β-D-pentofuranosyl-5-ethyl)uracil

5-Chloromercuri-2'-deoxyuridine was prepared from 2'-deoxyuridine (10 g, 0.044 moles) by the procedure of Bergstron and Ruth (J. Carb. Nucl, and Nucl., 4,257, (1977)). 2'-Deoxy-5-ethyluridine was prepared by the method of Berstrom et al., (J. Am. Chem. Soc., 100, 8106, (1978)). The 5'-hydroxyl group was protected by the method of Example 62. The 3'-hydroxyl group was chlorinated and the 5'-hydroxyl was deprotected by the method of Example 64. The 3'-chloro of threo 3'-chloro-2',3'-dideoxyuridine was displaced with inversion of configuration by heating in HMPA with lithium azide (5 eq.) at 55° C. for one hour. The title compound was purified by chromatography on silica gel eluted with ethyl acetate. Removal of solvent from the appropriate fractions gave the desired compound; mp=112.5°-115° C.

EXAMPLE 66

1-(3'-Azido-2',3'-dideoxy-$\beta$-D-threo-pentofuranosyl)-5-(2-bromovinyl)uracil 5-Bromovinyl-2'-deoxyuridine (BVDU) was synthesized by the method of Jones, et al., (Tetrahedron Letters 45, 4415 (1979)) with similar yields. BVDU was tritylated and mesylated by the method of Horowitz et al. (J. Org. Chem., 31, 205 (1966)). This product (4.25 g, 6.5 mMol) was dissolved in 100 ml DMF containing 0.955 g (19.5 mMol) LiN$_3$ and heated at 74° C. for 24 hours. The reaction was poured onto 600 ml of ice with stirring. The solid which formed was isolated and purified by chromatography as a gum (2.48 g). Treatment by dissolution in 100 mL of 80% acetic acid and heating on a steam bath for 3 hours deblocked the compound. The cooled reaction was diluted with water and filtered to remove trityl carbinol. The filtrate was reduced in volume to an oil which was purified by flash chromatography in CHCl$_3$/CH$_3$OH (9:1 v/v). Combination of the appropriate fractions and removal of the solvent gave a solid which was crystallized twice from aqueous methanol. Yield 0.66 g, 1.8 mMol, 27.7%; mp 165°-166° C.

Analysis for C$_{11}$H$_{12}$BrH$_5$O$_4$-0.5H$_2$O Calculated: C, 35.98; H, 3.57; N, 19.07, Br, 21.85. Found: C, 35.98, H, 3.57; N, 19.07; Br 21.76.

EXAMPLE 67

1-(3'-Azido-2',3'-dideoxy-$\beta$-D-threo-pentofuranosyl)-5-methylisocytosine 1-(3'-Azido-2',3'-dideoxy-$\beta$-D-threo-pentofuranosyl)-2-methoxy-5-methyl-4(H)-pyrimidinone (0.5 g, 2 mMol) was combined with 15 mL of methanol saturated with ammonia in a bomb. After 6 days at ambient temperature the bomb was heated in an oil bath at 65° C. for 4 days. The reaction was taken to dryness and purified by crystallization from CHCl$_3$/CH$_3$OH (9:1 v/v). The solid was washed with CHCl$_3$ and air-dried to give 0.16 g, 0.6 mMol (30%) of product; mp 158°-160° C.

Analysis for C$_{10}$H$_{14}$N$_6$O$_3$¼H$_2$O Calc: C 44.36; H, 5.40; N, 31.04. Found: C, 44.42; H, 5.36; N, 31.04.

EXAMPLE 68

1-(3'-Azido-2',3'-dideoxy-$\beta$-D-threo-pentofuranosyl)-3-methyl thymine

5'-Trityl-3'-threo-3'-azido-3'-deoxythymidine (1.0 g, 1.95 mMol) and N,N-dimethylformamide dimethylacetal (Zemlicka, Coll. Czech. Chem. Comm., 35, 3572 (1972)) (0.93 g, 7.8 mMol) were refluxed in 50 mL CHCl$_3$ for 96 hours. Removal of the solvent gave an oil which was further purified by flash chromatography using CHCl$_3$. Removal of the solvent gave 0.54 g of a foam. Deblocking was conducted by heating the foam in 50 mL of 80% acetic acid on a steam bath for 2 hours. Trityl carbinol was removed by filtration after the reaction was diluted with H$_2$O. The filtrate was taken to an oil in vacuo and the oil was purified by flash chromatography using CHCl$_3$/EtOAc (2:1 v/v). The solvent was removed to give the compound as an oil, 0.20 g.

UV max (nm) at pH1 $\lambda$max=267 ($\epsilon$=8100), $\lambda$sh=209 ($\epsilon$=8500); at pH13 $\lambda$max=267 ($\epsilon$=8000).

H$^1$NMR (DMSO-d$_6$): $\delta$7.56 (s,1H,H6); $\delta$6.07 (dd,1H,H$_1$'); $\delta$3.17 (s,3H,N-CH$_3$); $\delta$1.86 (s,3H,5-CH$_3$).

Analysis for C$_{11}$H$_{15}$N$_5$O$_4$-0.4HOAc-0.3H$_2$O Calculated: C 45.62, H 5.58, N 22.54. Found: C 45.67, H 5.6, N 22.57.

EXAMPLE 69

(E)-3-[1-(3'-Azido-2',3'-dideoxy-$\beta$-D-erythro-pentofuranosyl)-1,2,3,4-tetrahydro-2,4-dioxo-5-pyrimidinyl]-2-propenoic Acid 2'-Deoxyuridine was converted to the 5-chloromercuri derivative according to the literature method, in 96% yield (Bergstrom and Ruth, J. Carb. Nucl., 4, 267, (1977)). This product (50 g; 1.04 mol) was dissolved in 800 mL dry MeOH containing ethyl acrylate (104 g; 1.04 mol) and a 0.1N solution of Li$_2$PdCl$_4$ in MeOH (1040 mL). The solution was stirred for 4 hours then treated with H$_2$S for 2 minutes. The suspension was filtered through a celite pad and the filtrate evaporated to dryness in vacuo. The residue was triturated with MeOH to yield a solid which was filtered and a dried to give 22 g of a white solid. This product was tritylated and mesylated by the method of Horowitz et.al. (J. Org. Chem., 31, 205 (1966)). A portion of this material (7.06 g; 10.9 mMol) was dissolved in 100 ml dry MeOH containing NaHCO$_3$ (0.92 g; 10.9 mMol) and refluxed for 6 hours. The solvents were removed in vacuo, the residue swirled with H$_2$O, then filtered and air-dried to give 6.1 g as a white solid. This product was dissolved in 50 mL DMF/1 ml H$_2$O containing LiN$_3$ (1.63 g; 33.2 mMol) and heated at 125° C. for 4 hours. The reaction was poured onto 200 ml ice, the precipitate collected and washed with H$_2$O. This material was then dissolved in 100 ml of 80% HOAC and heated at 100° C. for 4 hours. The reaction was diluted with H$_2$O and the precipitate filtered off. The filtrate was evaporated to dryness to give 800 mg of an oil. This oil was dissolved in 20 ml of 0.5N NaOH and stirred at ambient temperature for 2 hours. The solution was adjusted to pH 3, the precipitate filtered off and air-dried to give 550 mg (1.7 mMol) of the title compound: mp>250° C.

UV (nm): at pH1 $\lambda$max=300 ($\epsilon$=20400), $\lambda$min=230 ($\epsilon$=3900), $\lambda$sh=262 ($\epsilon$=13100) at pH13 $\lambda$max=297,266 ($\epsilon$=15600, 14800), $\lambda$min=281, 288 ($\epsilon$=13600, 8600);

H$^1$NMR (DMSO-d$_6$) $\delta$8.37 (s,1H,H6), $\delta$7.30 (s, 1H,—CH=, 5=15.57 Hz), $\delta$6.78 (d,1H, =CH—COOH, 5=15.93 Hz), $\delta$6.1-6.06 (m,1H,H1'), $\delta$5.41.5.37 (m, 1H,5'OH), $\delta$4.47-4.39 (m,1H,H3'), $\delta$3.87-3.83 (m,1H,H4), $\delta$3.74 3.58 (m, 2H,H5'), $\delta$2.54-2.81 (m,2H,H2').

Analysis for C$_{12}$H$_{13}$N$_5$O$_6$ Calculated: C 44.59, H 4.05, N 21.67. Found: C 44.45, H 4.06, N 21.60.

EXAMPLE 70

(E)-3-[1-(3'-Azido-2',3'-dideoxy-$\beta$-D-threo-pentofuranosyl)-1,2,3,4-tetrahydro-2,4-dioxo-5-pyrimidinyl]-2-propenoic Acid 2'-Deoxyuridine was converted to the 5-chloromercuri derivative, according to the literature method, in 96% yield (Bergstrom and Ruth, J. Carb. Nucl. Nucl, 4, 257 (1977)). This product (50 g 1.04 mol) was dissolved in 800 ml dry MeOH containing ethylacrylate (10.4 g, 1.04 mol) and a 0.1N solution of Li$_2$PdCl$_4$ in MeOH (10.40 ml). The solution was stirred for 4 hours then treated with H₂S for 2 minutes. The suspension was filtered through a celite pad and the filtrate evaporated to dryness in vacuo. The residue was triturated with MeOH to yield a solid which was filtered and air-dried to give 22 g of a white solid. This product was tritylated and mesylated by the method of Horowitz et al. (J. Org. Chem., 31, 205 (1966)). A portion of this material (2.7 g; 4.2 mMol) was dissolved in dry DMF (55 ml) containing LiN₃ (0.62 g; 12.7 mHol) and heated at 70° C. under N₂ for 24 hours. The reaction was poured onto 400 ml of ice, the precipitate collected and purified by flash chromatography. Elution with 50:1 CHCl₃/MeOH (v/v) gave 1.48 g of the azido intermediate. This material was treated with 50% acetic acid (100 mL) at 100° C. for 3 hours. Dilution with H₂O, filtration of the resulting suspension and evaporation of the filtrate in vacuo gave 710 mg of an oil. This oil was dissolved in 50 ml of NaOH and stirred at ambient temperature for 2 hours. The pH of the solution was brought to 3, the precipitate filtered off and air-dried to give 240 mg (0.7 mMol, 50%) of the title compound; mp=250° C.

UV(nm) at pH1 $\lambda$max=301 ($\epsilon$=19500), $\lambda$min=230 ($\epsilon$=3600), $\lambda$sh=249 ($\epsilon$=12700) at pH 13 $\lambda$max=299,267 ($\epsilon$=1400,13200), $\lambda$min=232,239 ($\epsilon$=1200, 7560]

H¹NMR (DMSO-d₆) $\delta$3.13 (s,7H,H6) $\delta$7.32 (d,1H,—CH=, $\delta$=15.87 Hz) $\delta$6.78(d,1H,=CH—COOH,J=15.62 Hz), $\delta$6.01–5.98 (m,1H,H1'), $\delta$5.11–5.98 (m,1H,5'OH), $\delta$4.50–4.43 (m,1H,H3'), $\delta$4.13–4.08 (m,1H,H4'), $\delta$3.80–3.75 (m,2H,H5'), $\delta$2.77–3.67 (m,1H,H3'), $\delta$2.30–2.20 (m,1H,H2').

Analysis for $C_{12}H_{13}N_5O_6 \cdot 1.5H_2O$ Calculated: C 41.15, H 4.60, N 19.99. Found: C 41.38, H 4.50, N 20.01.

EXAMPLE 71

(E)-3-[1-(3'-Azido-2',3'-dideoxy-β-D-erythro-pentofuranosyl)(2,3,4-tetrahydro-2,4-dioxo-5-pyrimidinyl]-2-propanoic acid The 5'-trityl-3'-mesyl-5-propenoate-2'-deoxyuridine was prepared according to the procedure of Example 69. This material was hydrogenated with 10% Pd/C in EtOH to give the propanoate derivative. This product was then treated in the manner described in the method above to give the title compound; mp=118°–120° C.

UV (nm): at pH1 $\lambda$max=265 ($\epsilon$=9900), $\lambda$min=235 ($\epsilon$=3100); at pH13 $\lambda$max=265 ($\epsilon$=7400), $\lambda$min=247 ($\epsilon$=5400);

H¹NMR (DMSO-d₆) $\delta$7.68 (s,1H,H6), $\delta$6.11–6.06 (m, 1H,H1'), $\delta$4.45–4.35 (m,1H,H3'), $\delta$3.85–3.80'm,1H,H4'), $\delta$3.68–3.53 (m,1H, H5')

Analysis for $C_{12}H_{15}N_5O_6$ Calculated: C 44.31, H 4.65, N 21.53. Found: C 44.26, H 4.68, N 21.49.

EXAMPLE 72

Clinical Study

3'-Azido-3'-deoxythymidine (AZT) was administered orally to 2 AIDS patients at a dose of 2 mg/kg every 8 hours on days 1 and 2 of treatment. On days 2 and 3 the patients were also given 500 mg probenecid (PB) every 6 hours and a single dose of AZT was given on day 3. The peak ($C_{max}$) and trough ($C_{min}$) levels at AZT on day 3 (after administration of probenecid) were significantly higher than the corresponding levels on day 1 resulting in a 3-fold decrease in the total body clearance (Cl/F) and a prolongation in the mean half-life (tl/2) of AZT (0.88 to 1.73 hr) during the PB treatment. The mean ratio of AZT glucuronide/AZT in the urine was markedly reduced from 7.3 to 2.4 after the PB treatment. The prinicpal pharmacokinetic parameters of AZT before and after coadministration of PB are summarised in Table 1.

TABLE 1

| Patient No. | AUC (hr* $\mu$m) | $C_{max}$ ($\mu$m) | $C_{min}$ ($\mu$m) | $T_{max}$ (hrs) | Cltot/F (ml/min/ 70 kg) | tl/2 (hrs) |
|---|---|---|---|---|---|---|
| 1. AZT/PB | 10.41 | 6.13 | 0.15 | 0.25 | 829.50 | 1.84 |
| 2. AZT/PB | 10.00 | 6.46 | 0.27 | 0.50 | 921.00 | 1.61 |
| MEAN ± | 10.21 | 6.30 | 0.21 | 0.38 | 875.25 | 1.73 |
| SD | 0.29 | 0.23 | 0.08 | 0.18 | 64.70 | 0.16 |
| 1. AZT | 3.70 | 3.74 | 0.00 | 0.50 | 2333.80 | 0.87 |
| 2. AZT | 3.04 | 2.51 | 0.00 | 0.31 | 3027.00 | 0.89 |
| MEAN ± | 3.37 | 3.13 | 0.00 | 0.41 | 2680.40 | 0.88 |
| SD | 0.47 | 0.87 | 0.00 | 0.13 | 480.17 | 0.01 |

EXAMPLE 73

Antiviral Activity

The enhancement of the Anti-Friend Leukemia Virus (FLV) activity of 3'-azido-3'-deoxythymidine (AZT) by the nucleoside transport inhibitors dipyridamole, dilazep and 6-[(4-nitrobenzyl)thio]-9-β-D-ribofuranosyl)purine is shown in Table 2. FG-10 cells were seeded on a plate one day before they were infected with FLV. One hour after infecting, known concentrations of the test compounds or combinations were added. The plates were incubated for 3 days, the media replaced with fresh McCoy's 5A media and incubated another 3 days. Concentrations of test compound/combinations giving 50% inhibition of plaques were determined as shown in Table 2. Neither dipyridamole (10 $\mu$M) nor dilazep (5 $\mu$M) alone had any observed antiviral effect.

TABLE 2

| Compound/Combination | Azidothymidine ED$_{50}$ (nM) |
|---|---|
| AZT | 5 |
| AZT + 1 $\mu$M dipyridamole | 1 |
| AZT + 5 $\mu$M dipyridamole | 0.5 |
| AZT + 10 $\mu$M dipyridamole | 0.2 |
| AZT + 5 $\mu$M dilazep | 0.5 |
| AZT + 5 $\mu$M 6-[(4-nitrobenzyl)thio]-9-β-D-ribofuranosyl)purine | 3 |

EXAMPLE 74

Anti-ITP Activity of 3'-Azido-3'-deoxythymidine (AZT)

A patient having a platelet count of 38,000 mm$^{-3}$ was diagnosed as having thrombocytopaenia purpura (platelet count <100,000 mm$^{-3}$) and was treated for 6 weeks with 5 mg/kg of AZT intravenously every 6 hours during which time, his platelet count rose to 140,000 mm$^{-3}$. Treatment was then changed to 5 mg/kg/4 hours orally for 4 weeks, discontinued for 4 weeks, when a drop in platelet numbers, to 93,000 mm$^{-3}$ after 2 weeks, and to 70,000 mm$^{-3}$ after 4 weeks, was seen. Treatment was recommenced at 5 mg/kg/4 hours orally for 5 weeks and the platelet count rose to 194,000 mm$^{-3}$. A reduction to 2.5 mg/kg/4 hours orally indefinitely resulted in a slight decrease in platelet count, but not to an extent diagnostic of ITP.

EXAMPLE 75

Treatment of Kaposis Sarcoma with
3'-Azido-3'-deoxythymidine (AZT)

In this study, 9 patients diagnosed as having Kaposi's sarcoma (KS) were treated with AZT and the following effects observed.
A complete cure was effected in one patient.
Three patients exhibited regression of lesions.
In 2 patients the KS remained stable.
In 3 patients lesions progressed.

The response of =50% is comparable to that obtained with treatment with the preferred current therapy for KS, recombinant a-interferon.

EXAMPLE 76

AZT/Acyclovir Combinations vs. HIV in Vitro

Using a method analogous to that of Example 79, combinations of AZT and acyclovir (ACV) were tested for in vitro efficacy vs. HIV.

ACV alone showed little activity, a concentration of 16 μg/ml (the highest tested) exhibiting less than 30% protection, while AZT at 8 μM demonstrated 100% protection by this method.

Table 3 shows those combinations of the two drugs required to achieve 100% protection.

TABLE 3

| ACV (μg/ml) | AZT (μM) |
|---|---|
| — | 0 |
| 8 | 0.5 |
| 2 | 1 |
| 1 | 4 |
| 0 | 8 |

These results indicate that ACV potentiates the antiviral activity of AZT about 3-fold.

EXAMPLE 77

AZT/Interferon Combinations vs. HIV in Vitro

Peripheral blood mononuclear cells (PBMC) from healthy HIV seronegative volunteer donors were obtained by Ficoll-Hypaque sedimentation of heparinized blood. Cells were treated with 10 μg/ml of phytohaemagglutinin (PHA) and grown in medium RPMI 1640 supplemented with 20% fetal calf serum (FCS), antibiotics, 1-glutamine and 10% interleukin-2 (IL-2) (Electronucleonics, Bethesda, Md.). From 4 to 6 days after exposure to PHA, cells were dispensed at concentrations of $4 \times 10^5$ cells/ml in 25 cm³ flasks containing 5 ml medium and then exposed to drugs and virus as detailed below. The day of virus inoculation is referred to as day 0. On day 4 fresh medium was added. Every 3 to 4 days thereafter, a portion of the cell suspension was removed for analysis and replaced with cell-free medium. Experiments 2 and 4 were terminated after 14 days and experiments 1 and 3 after 16 days.

Virus stocks were cell free supernatant fluids of HIV-infected H9 cells frozen in aliquots at −70° C. The 50% tissue culture infectious dose ($TCID_{50}$) of the virus stock was $10^5$/ml.

Four separate experiments were performed using PBMC from different donors (Table 4). In experiment 1, both drugs were added after cells had been exposed to virus. Aliquots of $40 \times 10^6$ cells were suspended in 20 ml of medium containing $10^5$ $TCID_{50}$ of virus for 1 hour, then washed 3 times and resuspended in virus free medium. In experiments 2 to 4, cells were incubated for 24 hours in medium with or without recombinant α interferon (rIFNαA), then exposed to AZT and virus. Virus was added directly to cultures in a small volume of medium and not washed off. The viral inocula were $4 \times 10^3$, $10^3$, and $2 \times 10^3$ $TCID_{50}$ in experiments 2, 3 and 4 respectively. Drug concentrations were adjusted at each medium change such that original concentrations were maintained.

In all experiments, serial two-fold dilutions of a fixed combination of rIFNαA and AZT were studied. Each concentration of rIFNαA and AZT used in combination was also studied alone to provide points of reference.

In all experiments, duplicate cultures were maintained for each concentration and for infected and uninfected controls. In experiment 1, 3.2 μM of AZT and 128 units/ml (U/ml) of rIFNαA, as well as 5 twofold dilutions of this combination, were studied.

In experiments 2 and 3, 0.16 μM AZT and 128 U/ml of rIFNαA, and 3-4 twofold dilutions of this combination, were employed. In experiment 4, 0.08 μM AZT together with 128 U/ml of rIFNαA, and 2 twofold dilutions of this combination, were employed.

After approximately one week, cultures were evaluated every 3 to 4 days for presence of virus. Cells were evaluated for HIV antigens by indirect immunofluorescence; supernatant fluids were evaluated for reverse transcriptase (RT) activity, virus yield, and for HIV p24 antigen by radioimmunoassay. The multiple drug effect analysis of Chou and Talalay (Advances in Enzyme Regulation, (1984), 22, 27-55) was used to calculate combined drug effects.

Data were also evaluated by the isobologram technique, a geometric method for assessing drug interactions. The concentration of AZT producing a desired (e.g. 50% inhibitory) effect is plotted on the horizontal axis, and the concentration of rIFNαA producing the same degree of effect is plotted on the vertical axis. A line is drawn connecting these points and the concentration of the agents in combination which produces the same effect is plotted. If this point falls below the line, the combination is considered synergistic.

In experiment 1, all concentrations of AZT were fully inhibitory, making it impossible to judge combined effects. In experiments 2-4, a synergistic interaction of the two agents was consistently observed (Tables 4-9). The synergism was evident by all measures of viral replication employed, and persisted even when the effect of rIFNαA alone was negligible. Synergy calculations were performed by applying the multiple drug effect analysis to RT data from experiments 2-4, virus yield data from experiment 2 and 3, and RIA data from experiment 4. The isobologram method also indicated synergism.

TABLE 4

| Experiment | HIV Inoculation Method[a] | HIV added ($TCID_{50}$) | Timing of Drug Addition | |
|---|---|---|---|---|
| | | | rIFNαA | AZT |
| 1 | A | $10^5$ | 0 | 0 |
| 2 | B | $4 \times 10^3$ | −24 hours | 0 |
| 3 | B | $10^3$ | −24 hours | 0 |
| 4 | B | $2 \times 10^3$ | −24 hours | 0 |

[a] method A: $40 \times 10^6$ cells were suspended in 20 ml of medium containing $10^5$ $TCID_{50}$ HIV for 1 hour at 37° C., then washed and resuspended.
method B: Indicated amount of virus was added to $2 \times 10^6$ cells in medium; cells were not subsequently washed.

TABLE 5
Experiment 2-Day 10
Effects of rIFNαA and AZT on mean reverse transcriptase values (cpm/10⁶ cells × 10³).

| AZT (μM) | rIFNαA (U/ml) | | | | | |
|---|---|---|---|---|---|---|
| | 0 | 8 | 16 | 32 | 64 | 128 |
| 0 | 205 | 173 | 150 | 193 | 169 | 151 |
| 0.01 | 159 | 85 | | | | |
| 0.02 | 110 | | 42 | | | |
| 0.04 | 71 | | | 10 | | |
| 0.08 | 31 | | | | 4 | |
| 0.16 | 7 | | | | | 1 |

TABLE 6
Experiment 3-Day 13
Effects of rIFNαA and AZT on mean RT values (cpm/10⁶ cells × 10³)

| AZT (μM) | rIFNαA (U/ml) | | | | |
|---|---|---|---|---|---|
| | 0 | 16 | 32 | 64 | 128 |
| 0 | 157 | 143 | 117 | 117 | 130 |
| 0.02 | 51 | 10 | | | |
| 0.04 | 10 | | 0 | | |
| 0.08 | 2 | | | 0 | |
| 0.16 | 5 | | | | 0 |

TABLE 7
Experiment 4-Day 11
Effects of rIFNαA and AZT on mean RT values (cpm/10⁶ cells × 10³).

| AZT (μM) | rIFNαA (U/ml) | | | |
|---|---|---|---|---|
| | 0 | 32 | 64 | 128 |
| 0 | 32 | 5 | 4 | 2 |
| 0.02 | 8 | 1 | | |
| 0.04 | 4 | | 0 | |
| 0.08 | 1 | | | 0 |

TABLE 8
Experiment 3-Day 13
Effects of rIFNαA and AZT on virus yield (TCID₅₀/ml).

| AZT (μM) | rIFNαA (U/ml) | | | | |
|---|---|---|---|---|---|
| | 0 | 16 | 32 | 64 | 128 |
| 0 | $10^{5.7}$ | $10^{5.6}$ | $10^{5.3}$ | $10^{5.1}$ | $10^{5.0}$ |
| .02 | $10^{4.8}$ | $10^{1.9}$ | | | |
| .04 | $10^{.3}$ | | $<10^{1.9}$ | | |
| .08 | $10^{1.9}$ | | | $<10^{1.9}$ | |
| .16 | $<10^{1.9}$ | | | | $<10^{1.9}$ |

TABLE 9
Experiment 4-Day 14
Effects of rIFNαA and AZT on HIV p24[a]

| AZT (μM) | IFNαA (U/ml) | | | |
|---|---|---|---|---|
| | 0 | 32 | 64 | 128 |
| 0 | 200–300 | 100–200 | 50–100 | 25–30 |
| 0.02 | 100–200 | 2.2 | | |
| 0.04 | 25–30 | | 1.0 | |
| 0.08 | 11.2 | | | 0.8 |

[a] HIV p24 levels are presented as ng protein/ml.

TABLE 10
Combination Indices for AZT and rIFNαA Calculated from RT Data.

| Experiment | Day in Culture | Combination Indices at Different Percentages of RT Inhibition | | |
|---|---|---|---|---|
| | | 50% | 90% | 95% |
| 2 | 7 | 2.14 | 0.34 | 0.23 |
| 2 | 10 | 0.37 | 0.30 | 0.28 |
| 3 | 6 | 0.26 | 0.73 | 1.39 |
| 3 | 13 | 0.12 | 0.15 | 0.17 |
| 3 | 16 | <0.01 | 0.02 | 0.05 |
| 4 | 8 | 0.01 | 0.03 | 0.04 |
| 4 | 14 | 0.02 | 0.07 | 0.12 |

C.I. values are determined by solving the equation for different degrees of RT inhibition. C.I. values <1 indicates synergism. The C.I. values given were obtained using the mutually non-exclusive form of the equation; values obtained using the mutually exclusive form were always slightly lower.

EXAMPLE 78

In Vitro Antibacterial Synergy Studies

3'-Azido-3'-deoxythymidine and 8 known antibacterial agents (listed in Table 11) were each treated with N,N-dimethylformamide for 30 minutes. Microtiter dilutions were prepared using Wellcotest broth.

Prior to synergy testing, MIC determinations were made for each compound individually against the test organism (*E. coli* CN314). Table 11 shows the MIC endpoints of each drug for *E. coli* CN314.

Two-fold serial dilutions of test drugs or 3'-azido-3'-deoxythymidine were prepared in "flat-bottom" or "transfer" microtiter plates, respectively. Plates containing the appropriate dilutions were combined, resulting in a series of 192 dilutions/combination. Controls consisting of compound alone were also included. The highest concentration of any drug used, was twice its MIC value (Table 11).

Test plates were inoculated with a bacterial seed culture containing approximately 5×10⁵ CFU/ml and were subsequently incubated at 27° C. for 18 hours. The wells were scored for bacterial growth or no growth, and the MICs determined. "Fractional inhibitory concentrations" (FICs) were calculated from MIC values by dividing the MIC in combination by the MIC of each single agent. The sum of the fractions (sum of the fractional inhibitory concentrations) was then calculated. A result of about 0.5, or less, is indictive of synergy.

TABLE 11
Minimal Inhibitory Concentrations (MIC's) of Test Drugs Alone

| Compound | MIC (μg/ml) |
|---|---|
| Tobramycin | 0.4 |
| Fusidic acid | 1000 |
| Chloramphenicol | 3.1 |
| Clindamycin | 100 |
| Erythromycin | 25 |
| Rifampicin | 6.2 |
| 3'-Azido-3'-deoxythymidine | 1.0 |
| Trimethoprim | 0.125 |
| Sulphadimidine | 32 |

Results of the synergy experiments are shown in Table 12.

TABLE 12

Synergy Studies: Combinations of AZT and Other Antibacterial Agents

| Combination | Optimal MIC's (µg/ml): Drug/AZT | FIC Index |
|---|---|---|
| Tobramycin/AZT | 0.2/0.125 | 0.25 |
| Fusidic acid/AZT | 250/0.03 | 0.28 |
| Chloramphenicol/AZT | 1.6/0.06 | 0.31 |
| Clindamycin/AZT | 12.5/0.25 | 0.375 |
| Erythromycin/AZT | 6.2/0.25 | 0.5 |
| Rifampicin/AZT | 3.1/0.06 | 0.56 |
| Trimethoprim/AZT | 0.004/0.5 | 0.504 |
| Sulfadimidine/AZT | 0.25/0.125 | 0.375 |

EXAMPLE 79

Anti-HIV Activity of 3'-Azidonucleosides in Vitro

In Vitro activity of 3'-azidonucleosides (drugs) was assayed in two cell-lines; H9 (OKT4+ T-cell line, permissive to HIV replication but partially resistant to the cytopathic effect of HIV) and TM3 (T-cell clone, specific to tetanus-toxoid, immortalised by lethally irradiated HTLV-I and selected for quick growth and sensitivity to the cytopathic effect of HIV).

The inhibitions assay was performed as follows: TM3 cells were stimulated by antigen-plus irradiated (4000 rad; 40 Gy) fresh autologous peripheral blood mononuclear cells (PBM) and cultured in complete medium containing 15% (v/v) interleukin 2 (IL-2, lectin-depleted; Cellular Products, Buffalo, N.Y.) 6 days before assay. ATH8 cells were used without the antigen stimulation. After pre-exposure to 2 µg of Polybrene per ml for 30 min, the target T-cells ($2 \times 10^5$) were pelleted, exposed to HIV for 45 min, resuspended in 2 ml of fresh medium, and incubated in culture tubes at 37° C. in 5% $CO_2$-containing humidified air. Control cells were treated similarly but were not exposed to the virus. The cells were exposed continuously to IL-2 and drug. When ATH8 cells were used in this assay system, five virus particles per cell were the minimum cytopathic dose of virus. In the cell cocuiture experiments, $5 \times 10^4$ lethally irradiated (10,000 rad) HIV RF-II-producing H9 cells or uninfected H9 cells were added to $2 \times 10^5$ target T cells. At various time points, the total viable cells were counted in ahaemocytometer under the microscope by the tryptan blue dye exclusion method.

Results are shown in Table 13.

TABLE 13

| Compound | $ED_{50}$ (µM) |
|---|---|
| 3'-Azido-2',3'-dideoxycytidine | 10 |
| 3'-Azido-5-bromo-2',3'-dideoxyuridine | 5 |
| 3'-Azido-5-bromo-2',3'-dideoxycytidine | 5 |
| (E)-3-[1-(3'-Azido-2',3'-dideoxy-β-D-erythro-pentofuranosyl)-1,2,3,4-tetrahydro-2,4-dioxo-5-pyrimidinyl]-2-propenoic Acid. | 100 |

EXAMPLE 80

In Vitro Antibacterial Activity of 3'-Azidonucleosides

Table 14 demonstrates the in vitro antibacterial activity of 3'-azidonucleosides in terms of Minimum Inhibitory Concentration (MIC) against various bacterial species.

The standard used was trimethoprim (TMP) and the medium used was Wellcotest sensitivity Test Agar plus 7% lysed horse blood.

TABLE 14

| Organism | MIC (µg/ml) Compound | | | | | | | | |
|---|---|---|---|---|---|---|---|---|---|
| | 1 | 2 | 3 | 4 | 5 | 6 | 7 | 8 | Stand |
| E. coli | 0.1>> | >100 | 10 | 0.1>> | 10 | 0.1>> | 10 | 10 | >100 |
| Salmonella typhimurium | 0.1>> | 10 | 10 | 0.1>> | >100 | 10 | 10 | >100 | 0.5 |
| Salmonella typhosa | 0.1>> | 0.1>> | 10 | 0.1>> | 0.1>> | 10 | 10 | 0.1>> | 0.1 |
| Entero. aerogenes | 0.1>> | 10 | >100 | >100 | 100 | 10 | 10 | >100 | 0.5 |
| Citro. freundii | 10 | 10 | 10 | 0.1>> | 10 | 10 | 10 | >100 | 0.5 |

Compounds used were:
1) 3'-Azido-3'-deoxy-4-thiothymidine
2) 3'-Azido-3'-deoxy-5'-O-acetyl-4-thiothymidine
3) 3'-Azido-3'-deoxy-2-deoxy-2-thiothymidine
4) 5'-Acetyl-3'-azido-3-benzoyl-3'-deoxythymidine
5) 1-(5'-O-Acetyl-3'-azido-2',3'-deoxy-β-D-erythro-pentofuranosyl)-5-methyl-4-(1,2,4-triazol-1-yl)-2(1H)-pyrimidinone
6) 1-(3'-Azido-2',3'-dideoxy-β-D-erythro-pentofuranosyl)-2-(benzyloxo)-5-methyl-4-(1H)-pyrimidinone
7) 3'-Azido-3'-deoxy-2-methoxythymidine
8) 3'-Azido-5-bromo-2',3'-dideoxyuridine

EXAMPLE 81

1-(3-Azido-2,3-Dideoxy-β-D-erythro-pentofuranosyl)-2-(Propylamino)-5-Methyl-4-(1H)-Pyrimidinone 2,5'-Anhydro-1-(3-azido-2,3-dideoxy-β-D-erythro-pentofuranosyl) thymine (0.5 g, 2 mMol) was refluxed in propylamine (20 mL) for 5 hours. The reaction was evaporated to an oil, triturated with MeOH (3×), then EtOAc (3×) and dried overnight under high vacuum to yield the title compound as a solid: mp=146° C.; UV(nm): at pH 1 λmax=263,226(ε=7600,11400), λmin=250(ε=6900); at pH 13 λmax=264(ε=5600), λmin=256(ε=5500); H NMR(DMSO-d6) δ7.5(s,1H,H6), 7.1(m,1H,—NH), 5.85(t,1H,H1',J=6.40 Hz), 5.4(broad s,1H,5'OH), 4.5–4.4(m,1H,H3'), 3.8–3.7(m,1H,H4'), 3.6(broad s,2H,H5'), 3.2–3.1(m,2-H,—NH—CH2—), 2.4–2.3(m,2H,H2'), 1.7(s,3H,5-CH3), 1.5–1.4(m,2H,—CH2—CH3), 0.9–0.8(m,3-H,—CH2—CH3).

Analysis calculated for C13H20N6O3.0.5MeOH: C 49.99, H 6.84, N 25.91. Found: C 49.88, H 6.57, N 25.89.

EXAMPLE 82

1-(5-O-Acetyl-3-Azido-2,3-Dideoxy-β-D-erythro-pentofuranosyl)-5-Methyl-4-(Thiomethyl)-2-(1H)-Pyrimidinone 5'-Acetyl-3'-azido-4-thiothymidine was dissolved in H2O and treated with 1 equivalent of MeI at 0° C. for 24 hours. The solvents were removed in vacuo and the residue chromatographed on silica gel eluted with 20:1 CHCl3-EtOAc (v/v). Combination and evaporation of appropriate fractions yielded the title compound as an oil: UV(nm): at pH 1 λmax=309,273(ε=9800,6600), $\lambda$min=285,240($\epsilon$=6300,1300), $\lambda$sh=343($\epsilon$=3500); at pH 13 $\lambda$max=307,274($\epsilon$=11300,8100), $\lambda$min=283,241($\epsilon$=7800,2500); H NMR(DMSO-d6) $\delta$7.7(s,1H,H6), 6.05(t,1H,H1',J=6.06 Hz), 4.5–4.4(m,1H,H3'), 4.4–4.3(m,2H,H5'), 4.1–4.0(m,1H,H4'), 2.5–2.4(m,2H,H2'), 2.45(s,3H,—SCH3), 2.04 and 1.98(2s,6H,acetyl,5-CH3).

Analysis calculated for C13H17N5O4S.0.75H2O: C 44.25, H 5.28, N 19.85, S 9.09. Found: C 44.41, H 5.02, N 19.80, S 9.03.

EXAMPLE 83

1-(3-Azido-2,3-Dideoxy-$\beta$-D-erythro-pentofuranosyl)-5-(Ethynyl)Uracil

The title compound was prepared in a manner analogous to the procedure described in (1). 5'-Acetyl-3'-azido-2',3'-dideoxy-5-iodouridine (0.4 g, 0.94 mMol) was dissolved in anhydrous, deoxygenated triethylamine (50 mL) and treated with trimethylsilyl acetylene (0.37 g, 3.8 mMol), bis(triphenylphosphine)palladium-(II)chloride (14 mg), and CuI (14 mg) at 55° C. under N2 for 4 hours. The reaction was evaporated to dryness and the residue dissolved in CHCl3. The CHCl3 was washed with 5% EDTA (2×25 mL) then H2O (1×25 mL) followed by drying over Na2SO4. The CHCl3 solution was filtered and evaporated to a solid which was dissolved in 0.5N NaOCH3 in MeOH (50 mL) at ambient temperature. After 1 hour the solution was neutralized DOW 50 H+, filtered and evaporated in vacuo. The residue was chromatographed on silica gel and eluted with 9:1 CHCl3/MeOH (v/v). Combination and evaporation of the appropriate fractions yields the title compound as a solid, 80 mg(0.29 mMol, 30%): mp=134°–136° C.; UV(nm): at pH 1 $\lambda$max=286,225($\epsilon$=11300,10700), $\lambda$min=251($\epsilon$=3100); at pH 13 $\lambda$max=282($\epsilon$=9700), $\lambda$min=255($\epsilon$=5000); H NMR(DMSO-d6) $\delta$11.6(s,1H,—NH), 8.26(s,1H,H6), 6.01(t,1H,H1',J=6.01 Hz), 5.35–5.30(m,1H,5'OH), 4.4–4.3(m,1H,H3'), 4.08(s,1H,C CH), 3.85–3.80(m,1H,H4'), 3.7–3.6(m,2H,H5'), 2.5–2.3(m,2H,H2').

Analysis calculated for C11H11N5O4.0.2H2O.0.5MeOH: C 46.53. H 4.55, N 23.59. Found: C 46.66, H 4.26, N 23.62.

(1) M. J. Robins and P. J. Barr J. Org. Chem. 48, 1854(1983)

EXAMPLE 84

1-(3-Azido-2,3-Dideoxy-$\beta$-D-erythro-pentofuranosyl)-5-Methyl-4-(Thiomethyl)-2-(1H)-Pyrimidinone 1-(5-O-Acetyl-3-azido-2,3-dideoxy-$\beta$-D-erythro-pentofuranosyl)-5-methyl-4-(thiomethyl)-2-(1H)-pyrimidinone (0.68 g, 2 mMol, EX.) was dissolved in NH3 saturated MeOH (10 mL) at ambient temperature for 3 hours. The solvents were evaporated in vacuo to yield the title compound as a solid: mp=117°–123° C.; UV(nm): at pH 1 $\lambda$max=310,272($\epsilon$=10500,7500), $\lambda$min=285,241($\epsilon$=7700,2400), $\lambda$sh=341($\epsilon$=5100); at pH 13 $\lambda$max=308,274($\epsilon$=12000,8500), $\lambda$min=279,241($\epsilon$=8300,2600); H NMR(DMSO-d6) $\delta$7.98(s,1H,H6), 6.01(t,1H,H1',J=5.86 Hz), 5.33–5.27(m,1H,5'OH), 4.37–4.34(m,1H,H3'), 3.90–3.87(m,1H,H4'), 3.71–3.61(m,2H,H5'), 2.42(s,3H,—SCH3), 2.39–2.33(m,2H,H2'), 1.96(s,3H,5-CH3).

Analysis calculated for C11H15N5O3S: C 44.44, H 5.08, N 23.55, S 10.78. Found: C 44.26, H 5.15, N 23.41, S 10.70.

EXAMPLE 85

1-(3-azido-2,3-dideoxy-$\beta$-D-erythro-pentofuranosyl)-1,2,3,4-tetrahydro-2,4-dioxo-5-pyrimidinecarbonitrile 5'-Acetyl-3'-azido-2',3'-dideoxy-5-iodouridine(0.5 g, 1.2 mMol, Ex.) was treated with KCN(0.1 g, 1.6 mMol) and KOAc(0.15 g, 1.6 mMol) in anhydrous DMSO at 105° C. for 90 minutes in a method analogous to (1). The DMSO was evaporated in vacuo and the residue chromatographed on silica gel, eluted with CHCl3 then with 20:1 CHCl3/MeOH (v/v). Collection of appropriate fractions followed by evaporation of the solvents gave pure 5'-acetyl-3'-azido-5-cyano-2',3'-dideoxyuridine. This material was dissolved in NH3 saturated MeOH at ambient temperature and allowed to stand overnight. The solvents were evaporated in vacuo and the residue chromatographed on silica gel using 9:1 CHCl3/MeOH (v/v) as the eluting solvent. Collection and evaporation of the appropriate fractions yielded the title compound as a clear oil: UV(nm): at pH 1 $\lambda$max=276,214 ($\epsilon$=13700,12800), $\lambda$min=238 ($\epsilon$=2200); at pH 13 $\lambda$max=275 ($\epsilon$=10000), $\lambda$min=245($\epsilon$=3200); H NMR(DMSO-d6) $\delta$8.81(s,1H,H6), 5.95(dd,1H,H1',J=2.34,4.11 Hz), 5.45(t,1H,5'OH,J=5.08 Hz), 4.4–4.3(m,1H,H3'), 3.9–3.8(m,1H,H4'), 3.8–3.5(m,2H,H5'), 2.45–2.30(m,2H,H2').

Analysis calculated for C10H10N6O4.1.25H2O.0.4EtOAc: C 41.47, H 4.71, N 25.01. Found: C 41.33, H 4.52, N 24.74.

(1) P. F. Torrence et. al. J. Med. Chem. 20, 974 (1977).

EXAMPLE 86

1-(5-O-Acetyl-3-Azido-2,3-Dideoxy-$\beta$-D-erythro-pentofuranosyl)-5-Methyl-4-(Propylamino)-2-(1H)-Pyrimidinone 1-(5-O-Acetyl-3-azido-2,3-dideoxy-$\beta$-D-erythro-pentofuranosyl)-5-methyl-4-(1,2,4-triazol-1-yl)-2-(1H)-pyrimidinone (0.5 g, 1.4 mMol) was dissolved in dry CH3CN (50 mL) and treated with n-propylamine (0.6 mL, 7 mMol) at ambient temperature for 48 hours. The reaction was evaporated to an oil and chromatographed on silica gel eluted with 20:1 CHCl3/MeOH (v/v). The appropriate fractions were combined and evaporated to give the title compound as a solid: mp=138°–140° C.; UV(nm): at pH 1 $\lambda$max=285,217($\epsilon$=14900,12200), $\lambda$min=246($\epsilon$=2500); at pH 13 $\lambda$max=274($\epsilon$=12500), $\lambda$min=250($\epsilon$=9000), $\lambda$sh=236($\epsilon$=10000); H NMR(DMSO-d6) $\delta$7.32(s,1H,H6), 7.24–7.18(m,1-H,—NH—), 6.13(t,1H,H1',J=6.44 Hz), 4.45–4.40(m,1H,H3'), 4.23–4.21(m,2H,—NH—CH2—), 4.00–3.92(m,1H,H4'), 3.26–3.19(m,2H,H5'), 2.33–2.26(m,2H,H2'), 2.05(s,3H,acetyl), 1.85(s,3H,5-CH3), 1.57–1.46(m,2H,—CH2—CH3), 0.88–0.81(t,3-H,—CH2—CH3).

Analysis calculated for C15H22N6O4: C 51.42, H 6.33, N23.99. Found: C 51.48, H 6.34, N 23.99.

EXAMPLE 87

1-(3-Azido-2,3-Dideoxy-β-D-erythro-pentofuranosyl)-5-Methyl-4-(Propylamino)-2-(1H)-Pyrimidinone 1-(5-O-Acetyl-3-azido-2,3-dideoxy-β-D-erythro-pentofuranosyl)-5-methyl-4-(propylamino)-2-(1H)-pyrimidinone (0.3 g, 0.8 mMol,EX.) was dissolved in NH3 saturated MeOH (15 mL). After 3 hours the solvents were evaporated in vacuo to yield the title compound as a solid: mp=59°-62° C.; UV(nm): at pH 1 λmax=288,219(ε=11300,9500), λmin=247(ε=1700); at pH 13 λmax=276(ε=9000), λmin=253(ε=6400); H NMR(DMSO-d6) δ7.54(s,1H,H6), 7.17(t,1H,—NH—), 6.08(t,1H,H1',J=6.45 Hz), 5.17(t,1H,5'OH), 4.33(q,1H,H3'), 3.79(q,1H,H4'), 3.65-3.55(m,2H,—NH—CH2—), 3.26-3.19(m,2H,H5'), 2.22(t,2H,H2'), 1.83(s,3H,5-CH3), 1.6-1.4(m,2H,—CH2—CH3), 0.84(t,3H,—CH2—CH3).

Analysis calculated for C13H20N6O4.0.25H2O: C 49.91, H6.60, N 26.86. Found: C 49.84, H 6.64, N 26.62.

EXAMPLE 88

1-(3-Azido-2,3-Dideoxy-β-D-erythro-pentofuranosyl)-5-Methyl-2-Pyrimidinone 1-(5-O-Acetyl-3-azido-2,3-dideoxy-β-D-erythro-pentofuranosyl)-5-methyl-4-(1,2,4-triazol-1-yl)-2-(1H)-pyrimidinone (0.5 g, 1.4 mMol) was dissolved in CH3CN (10 mL) and treated with 85% hydrazine hydrate (0.105 g, 2.1 mMol) for 30 minutes at ambient temperature, analogous to the procedure described in (1). The solvents were evaporated in vacuo and the residue chromatographed on silica gel with 9:1 CHCl3/MeOH (v/v) as the eluting solvent. Collection and evaporation of appropriate fractions yielded a solid. The solid was dissolved in EtOH (50 mL) containing Ag2O (0.35 g, 1.5 mMol, 1.5 eq) and refluxed for 90 minutes. Filtration of the hot suspension through a bed of celite followed by removal of solvents in vacuo gave a solid. The solid was chromatographed on silica gel eluted with 20:1 CHCl3/MeOH (v/v). Combination and evaporation of appropriate fractions gave a solid which was dissolved in NH3 saturated MeOH (50 mL) for 3 hours. Evaporation of the solvents in vacuo yielded an oil which was chromatographed on silica gel eluted with 20:1 CHCl3/MeOH (v/v). The appropriate fractions were combined and solvents evaporated in vacuo to give an oil which slowly solidified upon standing: mp=62°-63° C.; UV(nm): at pH 1 λmax=326,212(ε=7700,13000), λmin=263(ε=200); at pH 13 λmax=322,218(ε=22700,10800), λmin=246(ε=400); H NMR(DMSO-d6) δ8.46(d,1H,H4,J=3.28 Hz), 8.23(d,1H,H6,J=3.23 Hz), 6.00(t,1H,H1',J=5.08 Hz), 5.31(t,1H,5'OH,J=5.12 Hz), 4.4-4.3(m,1H,H3'), 3.95-3.89(m,1H,H4'), 3.8-3.6(m,2H,H5'), 2.5-2.3(m,2H,H2'), 2.03(s,3H,5-CH3).

Analysis calculated for C10H13N5O3.0.25H2O: C 46.96, H 5.32, N 27.38. Found: C 47.05, H 5.40, N 27.14.

(1) D. Cech and A. Holy Coll. Czech. Chem. Comm. 42, 2246 (1977).

We claim:
1. 1-(3-azido-2,3-dideoxy-β-D-erythro-pentofuranosyl)-5-methyl-2-(propylamino)-4(1H)-pyrimidinone.

* * * * *